（12）United States Patent
Chang et al.

(10) Patent No.: US 8,951,938 B2
(45) Date of Patent: Feb. 10, 2015

(54) COMBINATORIAL ROSAMINE LIBRARY TO DETECT CELL-STATE SWITCHING

(75) Inventors: Young-Tae Chang, Singapore (SG);
Young-Hoon Ahn, New York, NY (US);
Yun Kyung Kim, Singapore (SG);
Bridget Wagner, Medford, MA (US);
Hyman A. Carrinski, Cambridge, MA (US); Paul Clemons, Medford, MA (US); Stuart Schreiber, Boston, MA (US)

(73) Assignees: New York University, New York, NY (US); President and Fellows of Harvard College, Cambridge, MA (US)

( * ) Notice: Subject to any disclaimer, the term of this patent is extended or adjusted under 35 U.S.C. 154(b) by 1453 days.

(21) Appl. No.: 12/340,933

(22) Filed: Dec. 22, 2008

(65) Prior Publication Data
US 2009/0227467 A1 Sep. 10, 2009

Related U.S. Application Data

(60) Provisional application No. 61/015,570, filed on Dec. 20, 2007.

(51) Int. Cl.
*C40B 30/04* (2006.01)
*C40B 30/06* (2006.01)
*C12Q 1/02* (2006.01)
*G01N 33/50* (2006.01)

(52) U.S. Cl.
CPC ........ *G01N 33/5073* (2013.01); *G01N 33/5061* (2013.01); *Y10S 436/80* (2013.01)
USPC .................. 506/9; 506/10; 435/7.21; 435/29; 436/800

(58) Field of Classification Search
None
See application file for complete search history.

(56) References Cited

U.S. PATENT DOCUMENTS

| 8,026,110 | B2 | 9/2011 | Chang et al. |
|---|---|---|---|
| 2003/0166002 | A1 | 9/2003 | Chang et al. |
| 2004/0122009 | A1 | 6/2004 | Chang et al. |
| 2004/0166540 | A1 | 8/2004 | Wang et al. |
| 2004/0219669 | A1 | 11/2004 | Katsura |
| 2004/0225125 | A1 | 11/2004 | Chang |
| 2004/0265252 | A1 | 12/2004 | Orlow et al. |
| 2005/0019831 | A1 | 1/2005 | Chang |
| 2005/0054006 | A1 | 3/2005 | Chang et al. |
| 2005/0227293 | A1 | 10/2005 | Chang |
| 2006/0293325 | A1 | 12/2006 | Chang et al. |
| 2007/0087435 | A1 | 4/2007 | Skorecki et al. |
| 2008/0064037 | A1 | 3/2008 | Chang et al. |
| 2008/0124751 | A1* | 5/2008 | Chang et al. .................. 435/29 |
| 2008/0160521 | A1 | 7/2008 | Chang et al. |
| 2009/0227467 | A1 | 9/2009 | Chang et al. |

FOREIGN PATENT DOCUMENTS

| WO | 2005033149 A1 | 4/2005 |
|---|---|---|
| WO | 2008115517 A2 | 9/2008 |
| WO | 2012027266 A2 | 3/2012 |

OTHER PUBLICATIONS

Summerhayes et al (1982 PNAS 79:5292-5296).*
Bilska et al (2005 Pharmacological Reports 57:570-77).*
Cho et al (2003 JBC 278:34823-33).*
Ahn et al., "Combinational Rosamine Library and Application to in Vivo Glutathione Probe," J. Am. Chem. Soc. 129:4510-11 (2007) (E-published Mar. 23, 2007).
Wagner et al., "Small-molecule Fluorophores to Detect Cell-state Switching in the Context of High-throughput Screening," J. Am. Chem. Soc. 130:4208-09 (2008) (E-published Mar. 8, 2008).
Wagner et al., "Supporting Information: Small-molecule Fluorophores to Detect Cell-state Switching in the Context of High-throughput Screening," available at http://pubs.acs.org/doi/suppl/10.1021/ja077656d?cookieSET=1.
Im et al., "A Fluorescent Rosamine Compound Selectively Stains Pluripotent Stem Cells," Angewandte Chemie Int. Ed. 49(41):7497-7500 (2010).
Im et al., "A Fluorescent Rosamine Compound Selectively Stains Pluripotent Stem Cells," Supporting Information, Angewandte Chemie (2010).
Chang et al., "Stem Cell Detection and Isolation Using Diversity Oriented Fluorescent Library Approach (DOFLA)," Poster Presentation, 8th ISSCR Annual Meeting, San Francisco, CA (Jun. 16-19, 2010).
Kang et al., "Stem Cell Detection and Isolation Using Diversity Oriented Fluorescent Library Approach (DOFLA)," Poster Presentation, 9th ISSCR Annual Meeting, Toronto, Canada (Jun. 15-18, 2011).

(Continued)

*Primary Examiner* — Samuel Woolwine
*Assistant Examiner* — Kaijiang Zhang
(74) *Attorney, Agent, or Firm* — LeClairRyan, a Professional Corporation

(57) ABSTRACT

The present invention relates to the use of rosamine derivative compounds, as described herein, in detecting differentiated forms of a cell type of interest in a sample and in screening for compounds which inhibit differentiation of the cell type of interest. The candidate compound has the following structure:

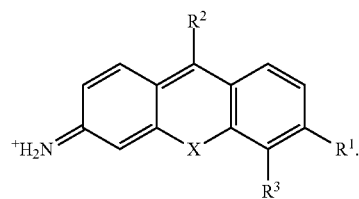

22 Claims, 32 Drawing Sheets

(56) References Cited

OTHER PUBLICATIONS

Kang et al., "Embryonic and Induced Pluripotent Stem Cell Staining and Sorting with the Live-Cell Fluorescence Imaging Probe CDy1," Nature Protocols 6(7):1044-1052 (2011).

Jiao et al., "Microwave-Assisted Syntheses of Regioisomerically Pure Bromorhodamine Derivatives," Organic Letters, 5:3675-3677 (2003).

Liu et al., "Ratonal Design and Synthesis of A Novel Class of Highly Fluorescent Rhodamine Dyes That Have Stong Absorption at Long Wavelengths," Tetrahedron Letters, 44:4355-4359 (2003).

Li et al., "Solid-Phase Synthesis of Styryl Dyes and Their Application as Amyloid Sensors," Angew Chem, Int. Ed., 43:6331-6335 (2004).

Müller et al., "Interactions of Heteroaromatic Compounds with Nucleic Acids," Eur. J. Biochem. 54:279-291 (1975).

International Search Report for related PCT International Patent Application No. PCT/US2011/048602 (mailed Aug. 22, 2011).

Kang et al., "Diversity-Driven Chemical Probe Development for Biomolecules: Beyond Hypothesis-Driven Approach," Chem. Soc. Rev. 40:3613-3626 (2011).

Kim et al., "Control of Muscle Differentiation by a Mitochondria-Targeted Fluorophore," with Supplementary Information, J. Am. Chem. Soc. 132(2):576-579 (published online Dec. 18, 2009).

\* cited by examiner

| CODE | λab(nm)[a] | λem(nm)[b] | PURITY(%)[c] | MASS[d] (CALC.) | MASS[e] (FOUND) | CODE | λab(nm)[a] | λem(nm)[b] | PURITY(%)[c] | MASS[d] (CALC.) | MASS[e] (FOUND) |
|---|---|---|---|---|---|---|---|---|---|---|---|
| A-1 | 505 | 550 | 88 | 305.1 | 305.3 | F-9 | 510 | 540 | 89 | 391.2 | 391.2 |
| A-2 | 500 | 550 | 90 | 330.2 | 330.3 | F-15 | 510 | 540 | 85 | 315.2 | 315.2 |
| A-3 | 500 | 550 | 91 | 317.1 | 317.3 | F-16 | 515 | 540 | 95 | 343.2 | 343.2 |
| A-4 | 495 | 530 | 91 | 379.1 | 379.4 | F-17 | 515 | 540 | 87 | 345.2 | 345.1 |
| A-5 | 500 | 550 | 93 | 303.1 | 303.1 | F-19 | 520 | 540 | 91 | 333.1 | 333.1 |
| A-6 | 525 | 540 | 91 | 327.0 | 327.1 | F-20 | 525 | 545 | 95 | 349.1 | 349.1 |
| A-7 | 500 | 550 | 91 | 337.2 | 337.3 | F-21 | 530 | 545 | 95 | 343.1 | 343.1 |
| A-8 | 505 | 535 | 91 | 333.1 | 333.3 | F-23 | 510 | 540 | 94 | 329.2 | 329.2 |
| A-9 | 490 | 550 | 93 | 363.1 | 363.3 | F-25 | 510 | 540 | 92 | 373.2 | 373.2 |
| A-10 | 505 | 550 | 94 | 339.1 | 339.3 | F-27 | 515 | 540 | 92 | 347.2 | 347.2 |
| A-11 | 525 | 550 | 88 | 387.1 | 387.1 | G-1 | 520 | 550 | 94 | 321.1 | 321.1 |
| A-12 | 510 | 535 | 93 | 341.1 | 341.3 | G-2 | 520 | 550 | 88 | 346.1 | 346.1 |
| A-13 | 500 | 550 | 91 | 367.1 | 367.4 | G-3 | 520 | 550 | 90 | 333.1 | 333.1 |
| A-15 | 500 | 550 | 93 | 287.1 | 287.2 | G-4 | 515 | 540 | 90 | 395.1 | 395.2 |
| A-16 | 500 | 550 | 94 | 315.1 | 315.2 | G-5 | 520 | 550 | 85 | 319.1 | 319.1 |
| A-17 | 500 | 550 | 92 | 317.1 | 317.2 | G-7 | 520 | 545 | 96 | 353.1 | 353.1 |
| A-18 | 500 | 550 | 90 | 331.1 | 331.3 | G-9 | 520 | 550 | 100 | 379.1 | 379.1 |
| A-19 | 500 | 550 | 90 | 305.1 | 305.1 | G-11 | 530 | 555 | 100 | 403.1 | 403.1 |
| A-20 | 505 | 535 | 91 | 321.1 | 321.1 | G-13 | 525 | 550 | 90 | 383.1 | 383.0 |
| A-21 | 505 | 535 | 86 | 315.1 | 315.1 | G-14 | 520 | 545 | 96 | 359.2 | 359.1 |
| A-22 | 505 | 550 | 85 | 442.2 | 442.2 | G-15 | 520 | 550 | 95 | 303.1 | 303.1 |
| A-23 | 500 | 530 | 91 | 301.1 | 301.2 | G-16 | 520 | 550 | 98 | 331.1 | 331.1 |

| CODE | λab(nm)a | λem(nm)b | PURITY(%)c | MASS d (CALC.) | MASS e (FOUND) | CODE | λab(nm)a | λem(nm)b | PURITY(%)c | MASS d (CALC.) | MASS e (FOUND) |
|---|---|---|---|---|---|---|---|---|---|---|---|
| A-24 | 500 | 530 | 98 | 347.1 | 347.1 | G-17 | 520 | 550 | 98 | 333.1 | 333.1 |
| A-25 | 500 | 530 | 92 | 345.2 | 345.2 | G-18 | 525 | 550 | 90 | 347.1 | 347.1 |
| A-26 | 505 | 530 | 90 | 335.1 | 335.1 | G-19 | 525 | 555 | 96 | 321.1 | 321.1 |
| A-27 | 500 | 530 | 90 | 319.1 | 319.1 | G-20 | 525 | 555 | 96 | 337.1 | 337.1 |
| A-29 | 500 | 530 | 94 | 329.2 | 329.2 | G-21 | 525 | 555 | 100 | 331.1 | 331.1 |
| B-1 | 530 | 565 | 97 | 333.1 | 333.1 | G-22 | 525 | 550 | 90 | 458.2 | 458.1 |
| B-2 | 525 | 565 | 94 | 358.2 | 358.2 | G-23 | 520 | 550 | 99 | 317.1 | 317.1 |
| B-3 | 525 | 565 | 92 | 345.2 | 345.2 | G-25 | 520 | 550 | 98 | 361.1 | 361.1 |
| B-4 | 525 | 570 | 90 | 407.2 | 407.1 | G-27 | 520 | 550 | 99 | 335.1 | 335.1 |
| B-7 | 525 | 570 | 93 | 365.2 | 365.1 | G-29 | 520 | 550 | 100 | 345.1 | 345.1 |
| B-8 | 525 | 570 | 93 | 361.1 | 361.1 | H-1 | 540 | 545 | 91 | 385.2 | 385.1 |
| B-9 | 505 | 570 | 91 | 391.2 | 391.2 | H-2 | 540 | 0 | 96 | 410.2 | 410.2 |
| B-10 | 530 | 570 | 92 | 367.1 | 367.1 | H-3 | 535 | 545 | 93 | 397.1 | 397.1 |
| B-11 | 545 | 565 | 89 | 415.1 | 415.1 | H-4 | 535 | 540 | 93 | 459.2 | 459.1 |
| B-13 | 520 | 570 | 92 | 395.2 | 395.2 | H-7 | 540 | 540 | 87 | 417.2 | 417.2 |
| B-14 | 525 | 565 | 95 | 371.2 | 371.2 | H-8 | 535 | 540 | 90 | 413.2 | 413.1 |
| B-15 | 525 | 570 | 94 | 315.1 | 315.2 | H-9 | 540 | 540 | 91 | 443.2 | 443.1 |
| B-16 | 525 | 565 | 94 | 343.2 | 343.2 | H-15 | 555 | 545 | 91 | 367.2 | 367.2 |
| B-17 | 525 | 565 | 96 | 345.2 | 345.2 | H-16 | 535 | 545 | 94 | 395.2 | 395.2 |
| B-18 | 530 | 565 | 89 | 359.1 | 359.1 | H-17 | 540 | 545 | 91 | 397.2 | 397.2 |
| B-19 | 530 | 570 | 93 | 333.1 | 333.2 | H-18 | 535 | 540 | 89 | 411.2 | 411.1 |
| B-20 | 530 | 570 | 88 | 349.1 | 349.1 | H-19 | 540 | 545 | 94 | 385.2 | 385.2 |

| CODE | λab(nm)a | λem(nm)b | PURITY(%)c | MASS d (CALC.) | MASS e (FOUND) | CODE | λab(nm)a | λem(nm)b | PURITY(%)c | MASS d (CALC.) | MASS e (FOUND) |
|---|---|---|---|---|---|---|---|---|---|---|---|
| B-21 | 535 | 580 | 95 | 343.1 | 343.1 | H-20 | 540 | 545 | 93 | 401.1 | 401.1 |
| B-22 | 530 | 570 | 98 | 470.2 | 470.2 | H-21 | 545 | 545 | 93 | 395.2 | 395.1 |
| B-23 | 525 | 565 | 90 | 329.2 | 329.2 | H-22 | 535 | 545 | 99 | 522.3 | 522.2 |
| B-24 | 525 | 560 | 96 | 375.2 | 375.1 | H-23 | 535 | 545 | 90 | 381.2 | 381.2 |
| B-25 | 525 | 565 | 92 | 373.2 | 373.2 | H-25 | 530 | 545 | 91 | 425.2 | 425.2 |
| B-26 | 530 | 560 | 94 | 363.2 | 363.1 | H-27 | 540 | 545 | 90 | 399.2 | 399.1 |
| B-27 | 525 | 565 | 94 | 347.2 | 347.1 | H-31 | 540 | 545 | 99 | 464.3 | 464.2 |
| B-28 | 545 | 575 | 99 | 321.1 | 321.1 | H-32 | 540 | 545 | 99 | 464.3 | 464.2 |
| B-29 | 525 | 565 | 92 | 357.2 | 357.2 | I-1 | 540 | 565 | 95 | 417.2 | 417.1 |
| B-30 | 530 | 570 | 87 | 414.2 | 414.2 | I-2 | 530 | 570 | 96 | 442.3 | 442.2 |
| B-31 | 530 | 570 | 91 | 412.2 | 412.2 | I-3 | 535 | 565 | 96 | 429.3 | 429.2 |
| B-32 | 530 | 570 | 92 | 412.2 | 412.2 | I-4 | 535 | 565 | 93 | 491.3 | 491.2 |
| B-33 | 530 | 570 | 90 | 398.2 | 398.2 | I-7 | 535 | 570 | 95 | 449.3 | 449.2 |
| C-1 | 535 | 575 | 99 | 373.2 | 373.2 | I-8 | 535 | 570 | 90 | 445.2 | 445.2 |
| C-2 | 535 | 575 | 98 | 398.2 | 398.2 | I-9 | 535 | 565 | 96 | 475.3 | 475.2 |
| C-3 | 535 | 570 | 95 | 385.2 | 385.2 | I-13 | 535 | 570 | 88 | 479.3 | 479.2 |
| C-4 | 532 | 570 | 97 | 447.2 | 447.1 | I-14 | 530 | 565 | 87 | 455.3 | 455.2 |
| C-7 | 535 | 575 | 93 | 405.2 | 405.2 | I-15 | 535 | 565 | 90 | 399.2 | 399.1 |
| C-8 | 535 | 575 | 92 | 401.2 | 401.1 | I-16 | 535 | 560 | 93 | 427.3 | 427.2 |
| C-9 | 530 | 570 | 93 | 431.2 | 431.2 | I-17 | 535 | 570 | 94 | 429.3 | 429.2 |
| C-13 | 535 | 575 | 97 | 435.2 | 435.2 | I-18 | 535 | 565 | 91 | 443.2 | 443.2 |
| C-15 | 535 | 575 | 90 | 355.2 | 355.2 | I-19 | 540 | 570 | 94 | 417.2 | 417.2 |

*FIG. 11 (cont'd)*

| CODE | λab(nm)[a] | λem(nm)[b] | PURITY(%)[c] | MASS[d] (CALC.) | MASS[e] (FOUND) | CODE | λab(nm)[a] | λem(nm)[b] | PURITY(%)[c] | MASS[d] (CALC.) | MASS[e] (FOUND) |
|---|---|---|---|---|---|---|---|---|---|---|---|
| C-16 | 530 | 570 | 91 | 383.2 | 383.2 | I-23 | 535 | 565 | 91 | 413.3 | 413.2 |
| C-17 | 535 | 575 | 93 | 385.1 | 385.2 | I-25 | 535 | 565 | 99 | 457.3 | 457.2 |
| C-18 | 535 | 575 | 91 | 399.2 | 399.1 | I-27 | 535 | 565 | 91 | 431.3 | 431.2 |
| C-19 | 540 | 575 | 95 | 373.2 | 373.1 | I-29 | 530 | 565 | 89 | 441.3 | 441.2 |
| C-20 | 540 | 575 | 94 | 389.1 | 389.1 | I-30 | 535 | 570 | 94 | 498.3 | 498.2 |
| C-21 | 540 | 585 | 90 | 383.2 | 383.1 | I-31 | 530 | 570 | 90 | 496.3 | 496.2 |
| C-22 | 535 | 570 | 95 | 510.3 | 510.2 | I-32 | 540 | 575 | 91 | 496.3 | 496.3 |
| C-23 | 535 | 570 | 92 | 369.2 | 369.2 | J-1 | 505 | 550 | 93 | 412.2 | 412.2 |
| C-24 | 535 | 570 | 99 | 415.2 | 415.1 | J-2 | 495 | 0 | 100 | 437.3 | 437.2 |
| C-25 | 530 | 560 | 93 | 413.2 | 413.2 | J-3 | 500 | 555 | 99 | 424.2 | 424.2 |
| C-26 | 540 | 570 | 91 | 403.2 | 403.1 | J-4 | 500 | 540 | 95 | 486.3 | 486.2 |
| C-27 | 535 | 570 | 90 | 387.2 | 387.1 | J-7 | 500 | 565 | 94 | 444.2 | 444.2 |
| C-29 | 530 | 570 | 95 | 397.2 | 397.2 | J-8 | 500 | 590 | 97 | 440.2 | 440.2 |
| C-30 | 535 | 560 | 97 | 454.3 | 454.2 | J-9 | 510 | 540 | 93 | 470.3 | 470.2 |
| C-31 | 540 | 565 | 96 | 452.3 | 452.2 | J-10 | 500 | 550 | 93 | 446.2 | 446.1 |
| C-32 | 540 | 565 | 98 | 452.3 | 452.2 | J-12 | 505 | 550 | 98 | 448.2 | 448.1 |
| D-7 | 500 | 530 | 88 | 338.1 | 338.1 | J-13 | 505 | 545 | 96 | 474.3 | 474.2 |
| D-8 | 500 | 530 | 96 | 334.1 | 334.1 | J-14 | 500 | 550 | 97 | 450.3 | 450.2 |

*FIG. 11 (cont'd)*

| CODE | λab(nm)a | λem(nm)b | PURITY(%)c | MASS d (CALC.) | MASS e (FOUND) | CODE | λab(nm)a | λem(nm)b | PURITY(%)c | MASS d (CALC.) | MASS e (FOUND) |
|---|---|---|---|---|---|---|---|---|---|---|---|
| D-9 | 500 | 535 | 90 | 364.1 | 364.1 | J-15 | 500 | 550 | 91 | 394.2 | 394.2 |
| D-13 | 500 | 530 | 96 | 368.1 | 368.1 | J-16 | 505 | 565 | 96 | 422.3 | 422.2 |
| D-17 | 500 | 530 | 92 | 318.1 | 318.1 | J-17 | 500 | 575 | 93 | 424.2 | 424.2 |
| D-18 | 500 | 530 | 90 | 332.1 | 332.1 | J-18 | 505 | 605 | 94 | 438.2 | 438.2 |
| D-23 | 490 | 525 | 95 | 302.1 | 302.1 | J-19 | 500 | 555 | 94 | 412.2 | 412.2 |
| D-25 | 495 | 525 | 90 | 346.1 | 346.1 | J-23 | 500 | 560 | 92 | 408.2 | 408.2 |
| D-27 | 495 | 530 | 91 | 320.1 | 320.1 | J-25 | 505 | 565 | 89 | 452.3 | 452.2 |
| D-29 | 495 | 530 | 96 | 330.1 | 330.1 | J-27 | 500 | 575 | 94 | 426.2 | 426.2 |
| E-1 | 490 | 545 | 90 | 346.2 | 346.2 | J-28 | 515 | 565 | 93 | 400.2 | 400.1 |
| E-2 | 480 | 550 | 92 | 371.2 | 371.2 | J-29 | 500 | 565 | 97 | 436.3 | 436.2 |
| E-3 | 485 | 545 | 93 | 358.2 | 358.2 | J-30 | 500 | 575 | 99 | 493.3 | 493.2 |
| E-4 | 480 | 545 | 90 | 420.2 | 420.2 | J-31 | 505 | 560 | 99 | 491.3 | 491.2 |
| E-7 | 485 | 545 | 86 | 378.2 | 378.2 | J-32 | 500 | 560 | 100 | 491.3 | 491.2 |
| E-8 | 485 | 550 | 95 | 374.2 | 374.1 | K-7 | 485 | 555 | 91 | 392.2 | 392.2 |
| E-9 | 485 | 550 | 91 | 404.2 | 404.2 | K-13 | 485 | 555 | 88 | 422.2 | 422.2 |
| E-10 | 495 | 550 | 91 | 380.1 | 380.1 | K-17 | 490 | 560 | 92 | 372.2 | 372.2 |
| E-13 | 475 | 540 | 98 | 408.2 | 408.2 | K-23 | 480 | 555 | 99 | 356.2 | 356.2 |
| E-14 | 480 | 550 | 92 | 384.2 | 384.2 | K-27 | 480 | 555 | 88 | 374.2 | 374.2 |

*FIG. 11 (cont'd)*

| CODE | λab(nm)a | λem(nm)b | PURITY(%)c | MASS d (CALC.) | MASS e (FOUND) | CODE | λab(nm)a | λem(nm)b | PURITY(%)c | MASS d (CALC.) | MASS e (FOUND) |
|---|---|---|---|---|---|---|---|---|---|---|---|
| E-15 | 485 | 550 | 88 | 328.2 | 328.2 | L-1 | 530 | 555 | 96 | 418.2 | 418.2 |
| E-16 | 480 | 545 | 87 | 356.2 | 356.2 | L-3 | 525 | 555 | 97 | 430.3 | 430.2 |
| E-17 | 490 | 545 | 90 | 358.2 | 358.2 | L-4 | 525 | 555 | 94 | 492.3 | 492.2 |
| E-18 | 485 | 550 | 85 | 372.2 | 372.2 | L-7 | 530 | 560 | 95 | 450.3 | 450.2 |
| E-19 | 485 | 545 | 91 | 346.2 | 346.1 | L-8 | 525 | 560 | 92 | 446.2 | 446.2 |
| E-20 | 485 | 550 | 89 | 362.1 | 362.1 | L-9 | 525 | 560 | 97 | 476.3 | 476.2 |
| E-21 | 490 | 545 | 92 | 356.2 | 356.2 | L-10 | 535 | 560 | 93 | 452.2 | 452.1 |
| E-23 | 485 | 545 | 99 | 342.2 | 342.2 | L-13 | 525 | 555 | 94 | 480.3 | 480.2 |
| E-24 | 486 | 545 | 95 | 388.2 | 388.1 | L-14 | 525 | 555 | 93 | 456.3 | 456.2 |
| E-25 | 480 | 545 | 98 | 386.2 | 386.2 | L-15 | 525 | 555 | 96 | 400.2 | 400.2 |
| E-26 | 485 | 545 | 85 | 376.2 | 376.1 | L-16 | 525 | 555 | 99 | 428.3 | 428.2 |
| E-27 | 480 | 545 | 94 | 360.2 | 360.2 | L-17 | 530 | 555 | 94 | 430.3 | 430.2 |
| E-29 | 485 | 550 | 89 | 370.2 | 370.2 | L-18 | 525 | 555 | 97 | 444.2 | 444.2 |
| F-1 | 515 | 540 | 91 | 333.1 | 333.2 | L-19 | 530 | 560 | 95 | 414.3 | 414.2 |
| F-3 | 510 | 540 | 94 | 345.2 | 345.1 | L-23 | 525 | 555 | 98 | 418.2 | 418.2 |
| F-4 | 500 | 540 | 95 | 407.2 | 407.1 | L-25 | 525 | 555 | 97 | 458.3 | 458.2 |
| F-7 | 510 | 540 | 88 | 365.2 | 365.2 | L-27 | 525 | 555 | 94 | 432.2 | 432.2 |
| F-8 | 505 | 545 | 90 | 361.1 | 361.1 | L-29 | 525 | 555 | 94 | 442.3 | 442.2 |

*FIG. 11 (cont'd)*

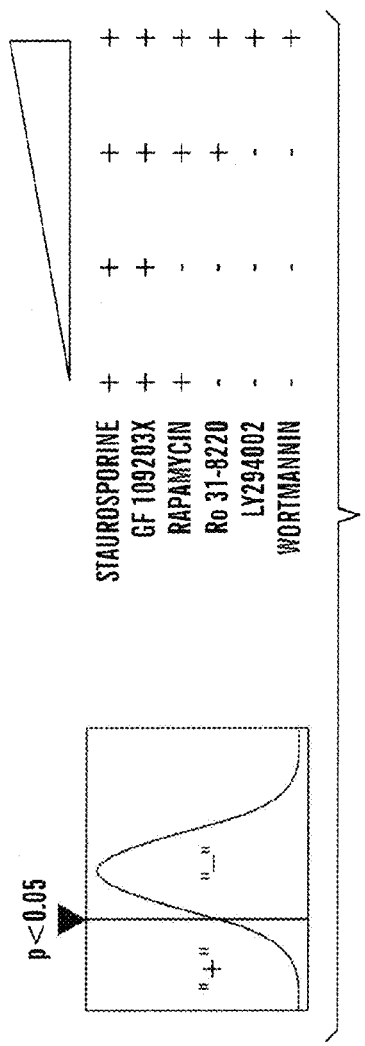
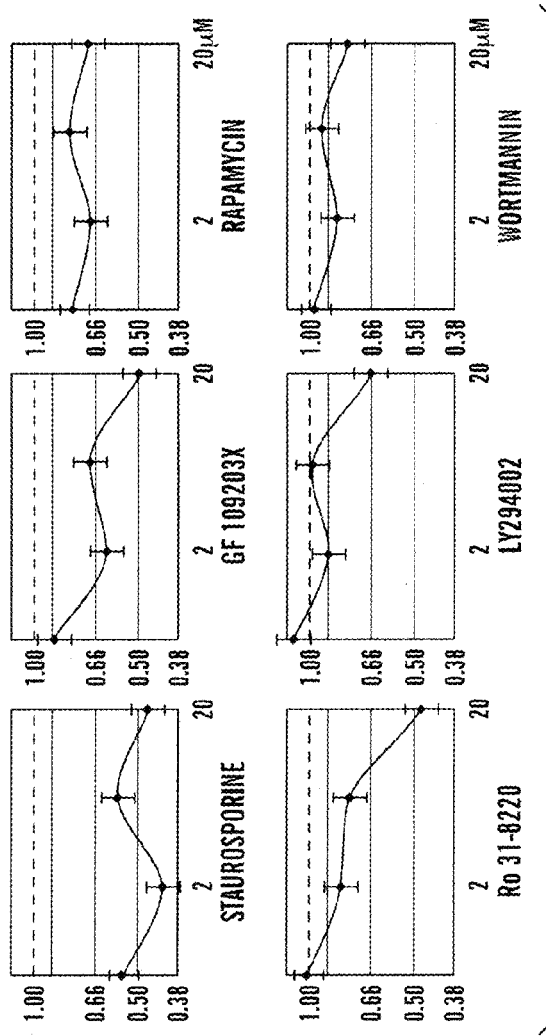
FIG. 17A
FIG. 17B

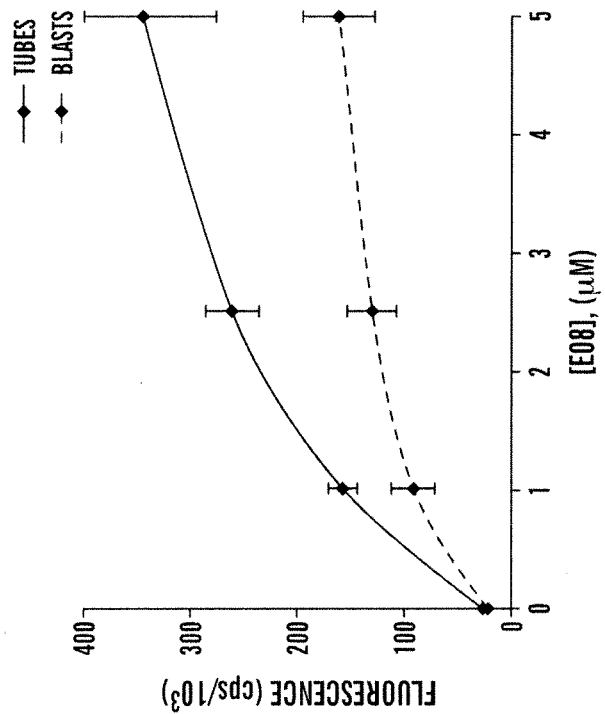
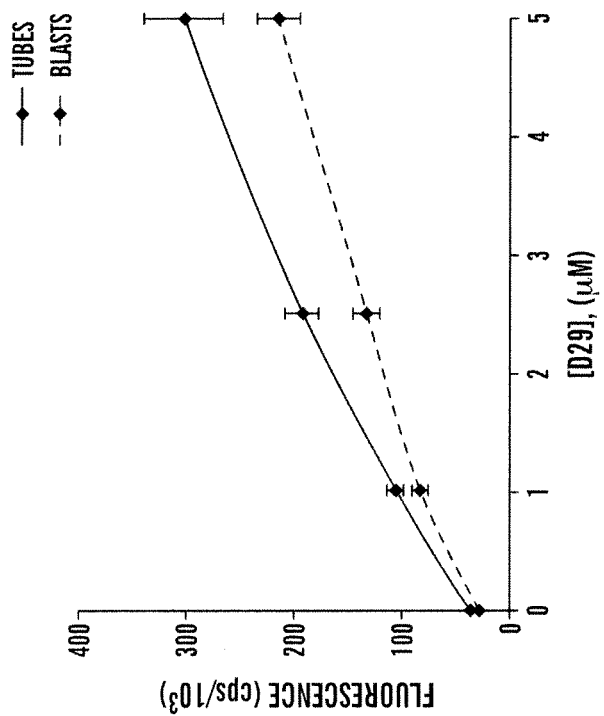
FIG. 20A
FIG. 20B

COMBINATORIAL ROSAMINE LIBRARY TO DETECT CELL-STATE SWITCHING

This application claims the benefit of U.S. Provisional Patent Application Ser. No. 61/015,570, filed Dec. 20, 2007, which is hereby incorporated by reference in its entirety.

This invention was made with government support under grant number 1P20GM072029-01 awarded by National Institutes of Health National Institute of General Medical Sciences. The government has certain rights in this invention.

FIELD OF THE INVENTION

The present invention is directed to a combinatorial rosamine library to detect cell-state switching.

BACKGROUND OF THE INVENTION

Fluorescent compounds have been excellent tools for the sensitive and specific detection of a variety of analytes (De Silva et al., "Signaling Recognition Events with Fluorescent Sensors and Switches," Chem Rev 97:1515-1566 (1997)). While the rational approach in designing the fluorescent sensors was successful toward diverse small molecule analytes (Gabe et al., "Highly Sensitive Fluorescence Probes for Nitric Oxide Based on Boron Dipyrromethene Chromophore-Rational Design of Potentially Useful Bioimaging Fluorescence Probe," J Am Chem Soc 126:3357-3367 (2004); Chang et al., "A Selective, Cell-Permeable Optical Probe for Hydrogen Peroxide in Living Cells," J Am Chem Soc 126:15392-15393 (2004); Burdette et al., "Fluorescent Sensors for Zn(2+) Based on a Fluorescein Platform: Synthesis, Properties and Intracellular Distribution," J Am Chem Soc 123:7831-7841 (2001); Schneider et al., "Coupling Rational Design with Libraries Leads to the Production of an ATP Selective Chemosensor," J Am Chem Soc 122:542-543 (2000)), the combinatorial approach to fluorescent dyes has shown powerful advantages owing to a wide range of spectral and structural diversity, developing specific binders for macromolecule structures with a concomitant change of fluorescence properties (Rosania et al., "Combinatorial Approach to Organelle-Targeted Fluorescent Library Based on the Styryl Scaffold," J Am Chem Soc 125:1130-1131 (2003); Lee et al., "Development of Novel Cell-Permeable DNA Sensitive Dyes Using Combinatorial Synthesis and Cell-Based Screening," Chem Commun (Camb) 15:1852-1853 (2003); Li et al., "Solid-Phase Synthesis of Styryl Dyes and Their Application as Amyloid Sensors," Angew Chem Int Ed Engl 43(46):6331-6335 (2004); Li et al., "RNA-Selective, Live Cell Imaging Probes for Studying Nuclear Structure and Function," Chem Biol 13(6):615-623 (2006)).

The identification of small molecules capable of detecting specific cellular states would facilitate high-throughput screening (Giepmans et al., Science 312:217-224 (2006); Zhang et al., Nat. Rev. Mol. Cell. Biol. 3:906-918 (2002); Finney, N. S., Curr. Opin. Chem. Biol. 10:237-245 (2006)). Many such probes are in current use, but the intended cell state difference is usually within the same cell type, with detection often dependent on either enzymatic or metabolic activity (Smiley et al., Proc. Natl. Acad. Sci. 88:3671-3675 (1991); Pendergrass et al., Cytometry A. 61:162-9 (2004)). A small molecule capable of distinguishing the distinct states resulting from cellular differentiation would be of enormous value, for example, in efforts aimed at regenerative medicine. One example is the use of hydrophobic dyes (Nile Red, Oil Red O) targeting the lipid droplets that accumulate during adipocyte differentiation (Fowler et al., Cytochem. 33:833-836 (1985)). Other cell models of differentiation require more complex measurements of cell state, such as gene expression (Stegmaier et al., Nat. Genet. 36:257-263 (2004); and Hieronymus et al., Cancer Cell. 10:321-330 (2006), which are hereby incorporated by reference in their entirety). Further, efforts toward the identification of fluorescent probes have focused on cell type-specific effects (Sweet et al., Biochem. Biophys. Res. Comm. 314:976-983 (2004)). In the case of myogenesis, a probe capable of distinguishing myoblasts from differentiated myotubes would represent a significant advance over current detection techniques, which typically involve immunofluorescence of proteins expressed selectively in the myotube state, and would facilitate the identification of small molecules involved in the differentiation process.

The present invention is directed to an improved class of fluorescent compounds.

SUMMARY OF THE INVENTION

The present invention relates to a method of detecting, in a sample, a cell type of interest and one or more differentiated forms of the cell type of interest. This method includes providing a sample potentially containing a cell type of interest and one or more differentiated forms of the cell type of interest and providing a rosamine derivative compound of the formula:

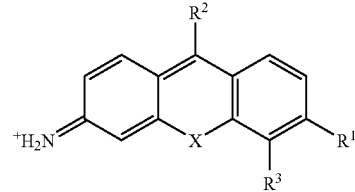

wherein:

X is O, $NR^4$, or S;

$R_1$ is $NR^4R^5$, OH, $NR^4R^6$, or

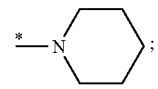

$R^2$ is substituted or unsubstituted phenyl, napthyl,

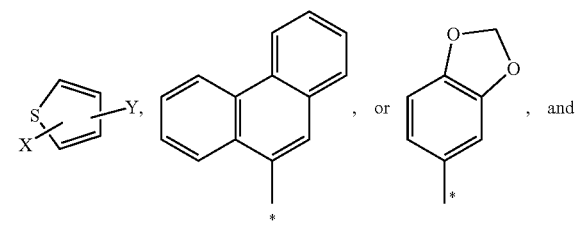

wherein the substituted form of $R^2$ has one or more substituents independently selected from the group consisting of halogen, $NR^4R^5$, $OR^7$, $SR^4$, aryl, $C_1$ to $C_6$ alkyl,

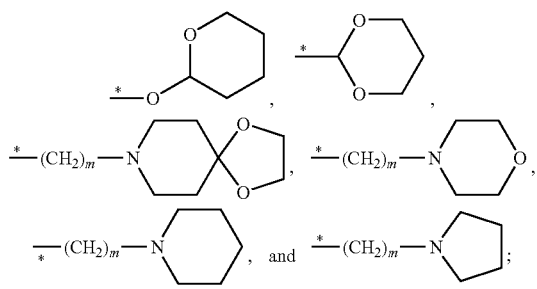

$R^3$ is H or with $R^1$ collectively forms a fused ring of the structure of

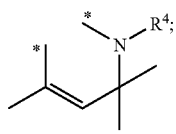

$R^4$ is H or $C_1$ to $C_6$ alkyl;
$R^5$ is H, $C_1$ to $C_6$ alkyl, or with $R^4$ collectively forms a ring structure;
$R^6$ is $(CH_2)_n NR^4 R^8$;
$R^7$ is H, $C_1$ to $C_6$ alkyl, or aryl;
$R^8$ is H or $C_1$ to $C_6$ alkyl;
Y is alkyl or halogen;
n is 1 to 3;
m is 0 to 3; and
* is a site on a substituent which binds to the rosamine derivative compound, where the rosamine compound produces differing fluorescent signals for the cell type of interest than for the one or more differentiated forms of the cell type of interest. The sample is with the rosamine derivative compound under conditions effective to produce differing fluorescent signals for the cell type of interest than for the one or more differentiated forms of the cell type of interest, if present in the sample. The presences of the cell type of interest and the one or more differentiated forms of the cell type of interest is detected based on fluorescent signals emitted by the sample following the contacting step.

Another aspect of the present invention relates to a method of screening for compounds which inhibit differentiation of a cell type of interest to one or more differentiated forms of the cell type of interest. This method includes providing a sample containing a cell type of interest and providing a rosamine derivative compound of the formula:

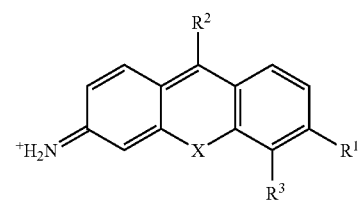

wherein:
X is O, $NR^4$, or S;
$R_1$ is $NR^4 R^5$, OH, $NR^4 R^6$, or

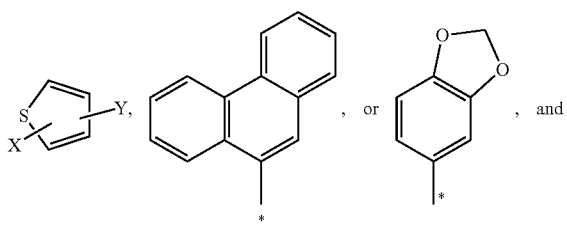

$R^2$ is substituted or unsubstituted phenyl, napthyl,

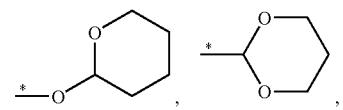

wherein the substituted form of $R^2$ has one or more substituents independently selected from the group consisting of halogen, $NR^4 R^5$, $OR^7$, $SR^4$, aryl, $C_1$ to $C_6$ alkyl,

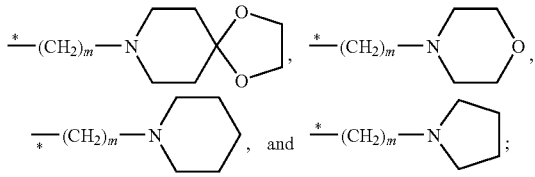

$R^3$ is H or with $R^1$ collectively forming a fused ring of the structure of

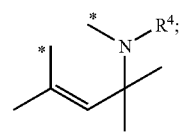

$R^4$ is H or $C_1$ to $C_6$ alkyl;
$R^5$ is H, $C_1$ to $C_6$ alkyl, or with $R^4$ collectively forms a ring structure;
$R^6$ is $(CH_2)_n NR^4 R^8$;
$R^7$ is H, $C_1$ to $C_6$ alkyl, or aryl;
$R^8$ is H or $C_1$ to $C_6$ alkyl;
Y is alkyl or halogen;
n is 1 to 3;
m is 0 to 3; and
* is a site on a substituent which binds to the rosamine derivative compound, where the rosamine compound produces differing fluorescent signals for the cell type of interest than for the one or more differentiated forms of the cell type of interest. A candidate compound is also provided and the sample, the candidate compound, and the rosamine derivative compound are then contacted. The sample, prior to after said contacting, is subjected to conditions effective to cause the cell type of interest in the sample to undergo differentiation to the one or more differentiated forms of the cell type of interest. Candidate compounds which reduce fluorescent signal for differentiated forms of the cell type of interest are identified as having potential activity as inhibitors of differentiation of the cell type of interest.

Rhodamine is a highly favored scaffold for cellular imaging and small molecule analytes sensing, due to advantageous photophysical properties such as high extinction coefficient and quantum yield, low toxicity, high photostability and pH-insensitivity, and relatively long emission wavelength (>500 nm) (Haugland, R. P. *Handbook of Fluorescent Probes and Research Chemicals*, 9th ed.; Molecular Probes: Eugene, Oreg. (2002), which is hereby incorporated by reference in its entirety). Rhodamine derivatives are widely used for labeling DNA, RNA, and proteins, but often suffered fluorescence quenching when labeling on protein, (Haugland, R. P. *Handbook of Fluorescent Probes and Research Chemicals*, 9th ed.; Molecular Probes: Eugene, Oreg., 2002; Ravdin et al., "Fluorescent Tetramethyl Rhodamine Derivatives of Alpha-Bungarotoxin: Preparation, Separation, and Characterization," *Anal Biochem* 80:585-592 (1977), which are hereby incorporated by reference in their entirety), or almost no intensity change upon binding with peptide (Marks et al., "In Vivo Targeting of Organic Calcium Sensors via Genetically Selected Peptides," *Chem Biol* 11(3):347-356 (2004); Rozinov et al., "Evolution of Peptides that Modulate the Spectral Qualities of Bound, Small-Molecule Fluorophores," *Chem Biol* 5(12):713-728 (1998), which are hereby incorporated by reference in their entirety), probably due to its rigid core structure with a high quantum yield. Therefore, it is envisioned that the introduction of structural flexibility and diversity on the rhodamine scaffold would generate a set of sensor candidates of which fluorescence intensity can be controlled by a binding event. The first combinatorial approach to a rosamine library is reported here and the potential of this library to find a selective sensor to a specific analytes is demonstrated.

BRIEF DESCRIPTION OF THE DRAWINGS

FIGS. 6 A-D show the characterization of the specific rosamine molecule, A4 in Table 1.

FIG. 10 A-B shows the fluorescence response of the specific rosamine molecules (J and L in Table 1) toward different analytes.

FIG. 11 shows the absorbance, fluorescent wavelength, and purity for the library of rosamine derivative compounds of the present invention.

FIG. 14A shows cells stained with H22 (3 μM) for 15 min. FIG. 14B shows cells supplemented with lipoic acid (250 μM) for 48 hr and stained with H22 for 15 min. Subsequently, α-lipoic acid-supplemented cells stained with H22 was incubated with NMM (1 mM) (FIG. 14C) or Diamide (50 μM) (FIG. 14D) for 20 min at room temperature.

FIGS. 17A-F show the use of E26 in cell-based screening for inhibitors of muscle differentiation. C2C12 myoblasts were treated with a collection of diverse kinase inhibitors for 48 h, and stained with E26 after five days in cell culture. Selected compounds resulted in significantly decreased fluorescence (p<0.05; indicated by "+") at increasing compound concentrations (FIG. 17A). Full screening results are available in Supporting Information. Fold decrease in fluorescence as a result of treatment with selected kinase inhibitors was calculated as an arithmetic mean of per-plate ratios of a compound-treatment well (indicated as μM) and the mean of mock-treatment wells (FIG. 17B). Error bars represent the standard deviation of mock-treated wells (48 replicates), indicating the noise in the assay system. The dashed line in each graph represents a ratio of 1.0, in which fluorescence is unchanged from the mock treatments. Myosin heavy chain (MHC) immunofluorescence is shown in FIGS. 17C, D. 1-h E26 treatment of C2C12 myotubes is shown in FIGS. 17C, E and of myoblasts treated with 100 nM and 600 nM rapamycin during differentiation are shown, respectively, in FIGS. 17D and 17F). Scale bar=150 μm.

FIGS. 19A-F show histograms of fluorescence for each compound image represented in FIG. 18: compound D29 (FIG. 19A), compound E08 (FIG. 19B), compound E25 (FIG. 19C), compound E26 (FIG. 19D), compound E27 (FIG. 19E), and compound E23 (FIG. 19F). Cells were segmented by the Cell Scoring module (Molecular Devices, Sunnyvale, Calif.) using the DAPI channel (Hoechst staining) for nuclei and the FITC channel for green fluorescence. Green fluorescence, expressed as logarithm-transformed total intensities, was quantified in the immediate vicinity of each nucleus. Black bars represent myoblasts treated with 250 nM of each compound, and green bars represent myotubes under the same conditions.

FIGS. 20A-E show high-throughput dose-response analysis for rosamine fluorescence in myoblasts and myotubes: compound D29 (FIG. 20A), compound E08 (FIG. 20B), compound E25 (FIG. 20C), compound E26 (FIG. 20D), and compound E27 (FIG. 20E). Plate-reader fluorescence intensities of myoblasts and myotubes are shown for each concentration of rosamine tested, and reflect the mean and standard deviation of 192 wells of a 384-well plate. Note that E23 displayed no selectively at 1 μM, and was not pursued further.

FIG. 21A is a representative mock-treated (DMSO) well. FIG. 21B shows treatment with 2 μM iodotubericidin, a MAP kinase inhibitor. FIG. 21C depicts treatment with 600 nM wortmannin, a phosphatidylinositol 3-kinase inhibitor. FIG. 21D shows treatment with 600 nM rapamycin, an mTOR inhibitor. Scale bar=150 μm.

DETAILED DESCRIPTION OF THE INVENTION

Figure 1:
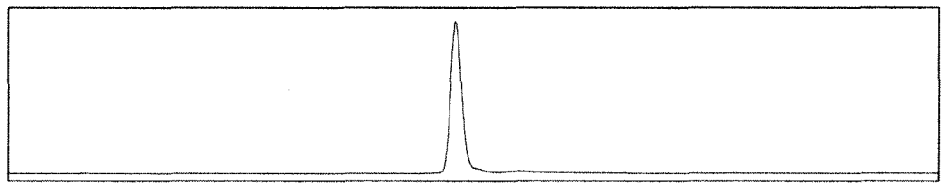
FIG. 1 shows the structure and HPLC trace of compound B1 in Table 1 (i.e. the rosamine derivative compound which is the reaction product of structure B from the listing of building block $T^1$ structures in Table 1 and structure 1 from the listing of $T^2$ structures in Table 1) in absorption of 500 nm and 250 nm and mass spectrum.
Figure 1:
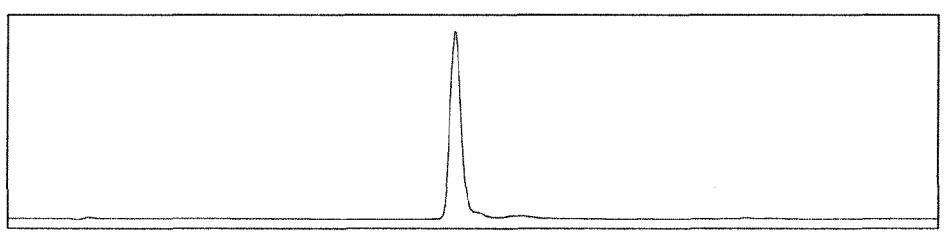
Figure 1:
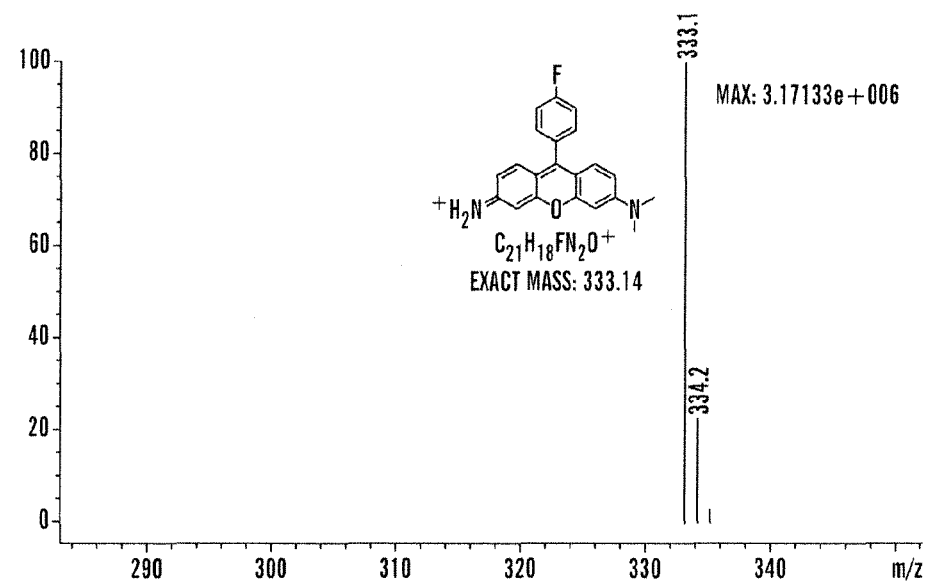
Figure 2:
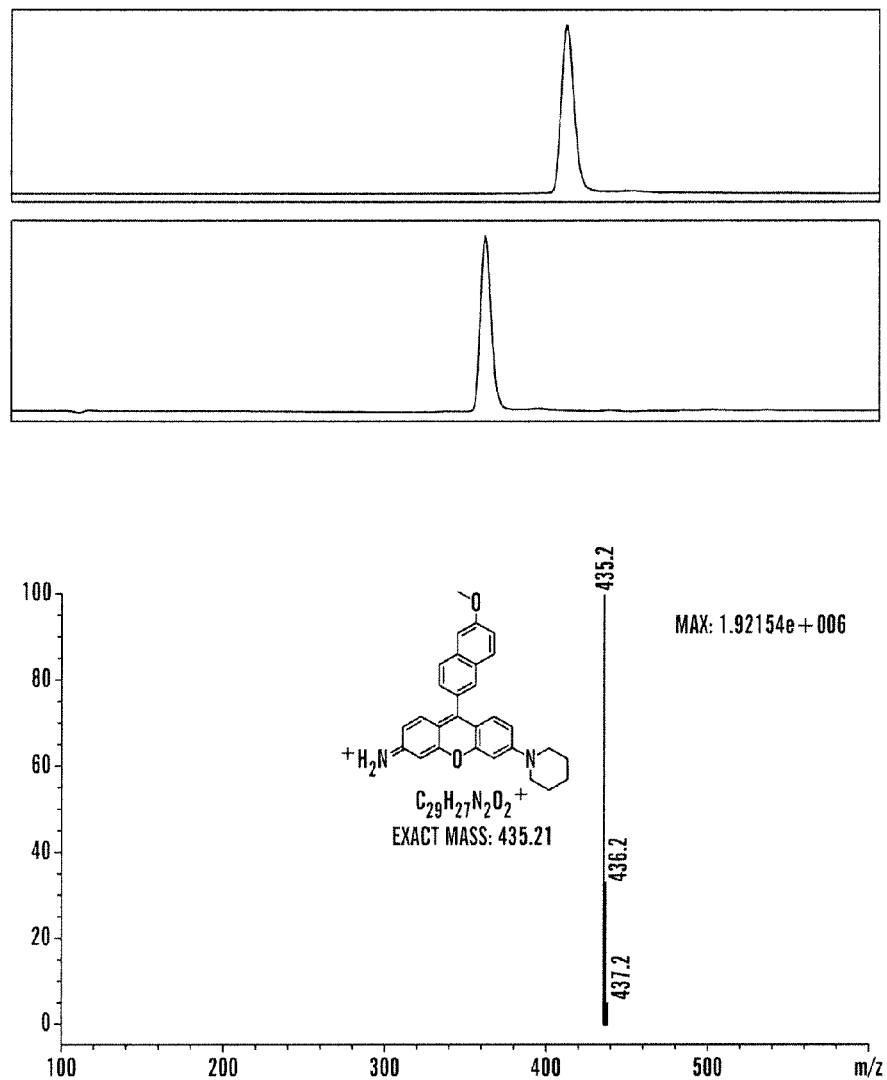
FIG. 2 shows the structure and HPLC trace of compound C13 in Table 1 in absorption of 530 nm and 250 nm mass spectrum.
Figure 3:
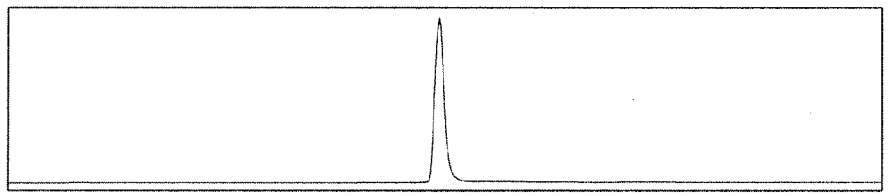
FIG. 3 shows the structure and HPLC trace of compound G9 in Table 1 in absorption of 520 nm and 250 nm mass spectrum.
Figure 3:
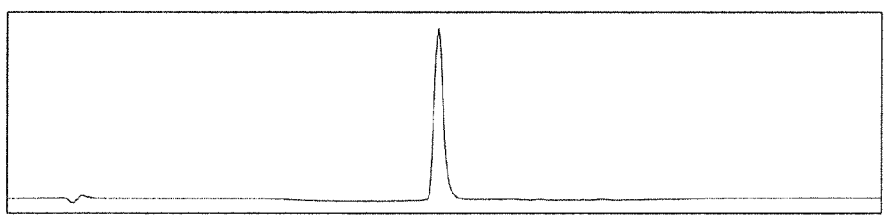
Figure 3:
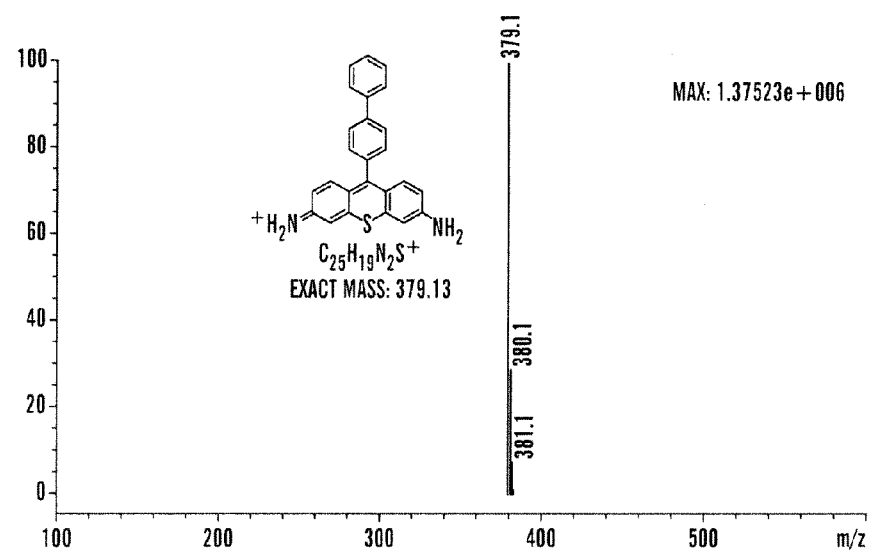
Figure 4:
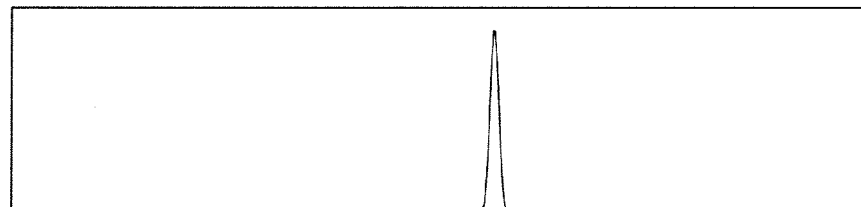
FIG. 4 shows the structure and HPLC trace of compound I25 in Table 1 in absorption of 480 nm and 250 nm mass spectrum.
Figure 4:
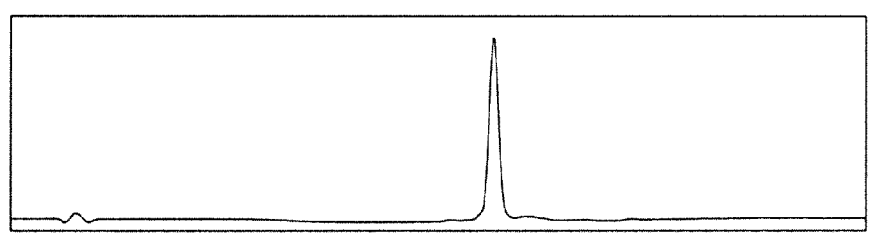
Figure 4:
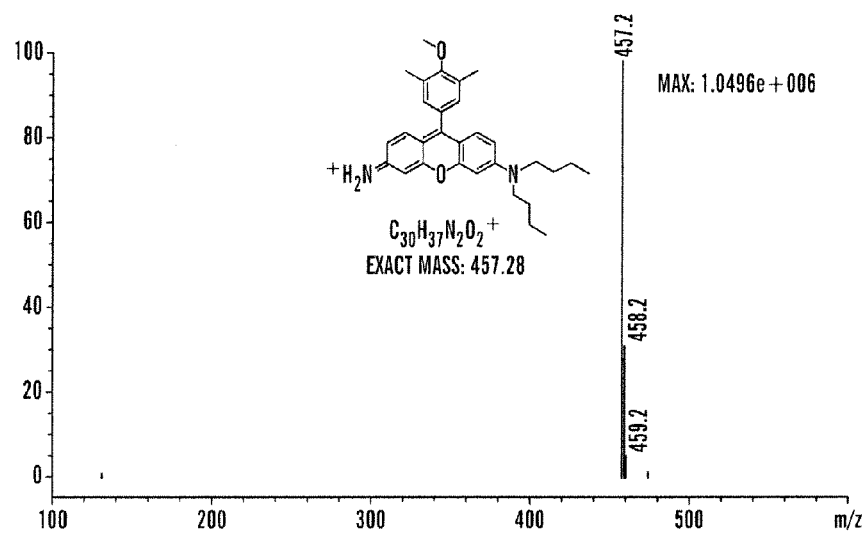
Figure 5:
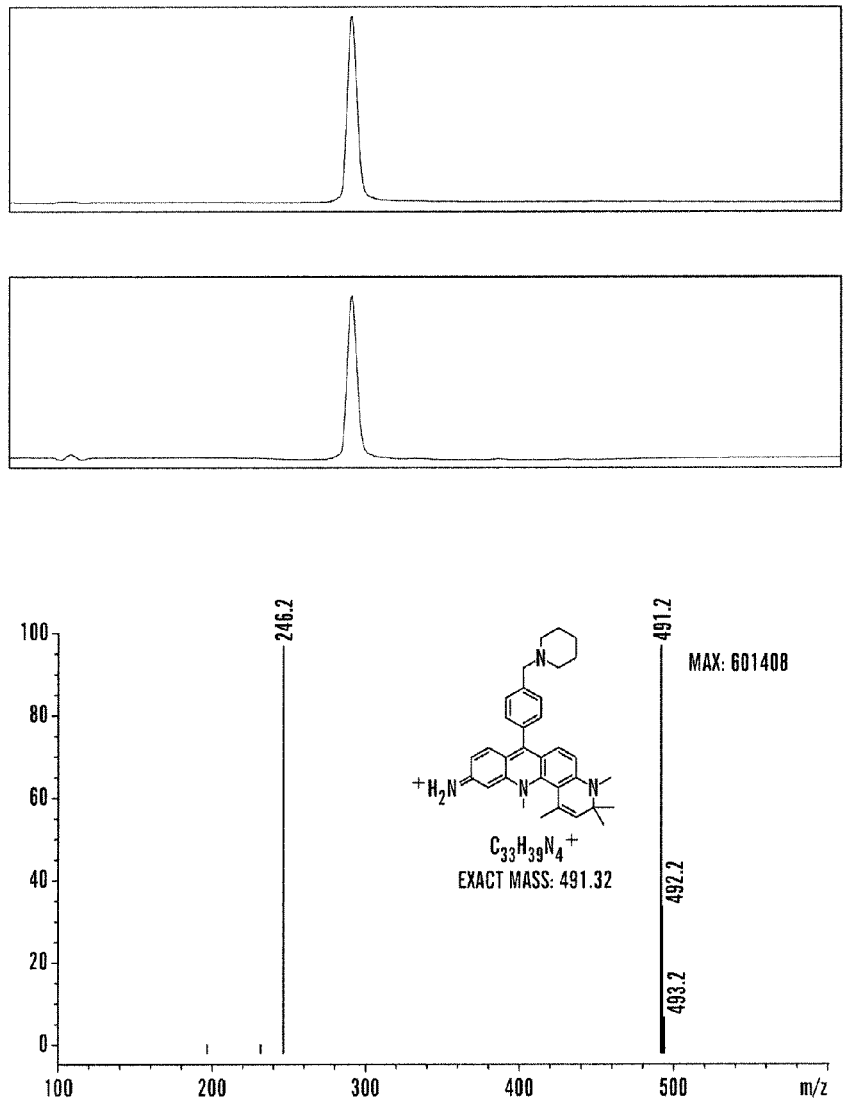
FIG. 5 shows the structure and HPLC trace of compound J32 in Table 1 in absorption of 530 nm and 250 nm mass spectrum.
Figure 6A:
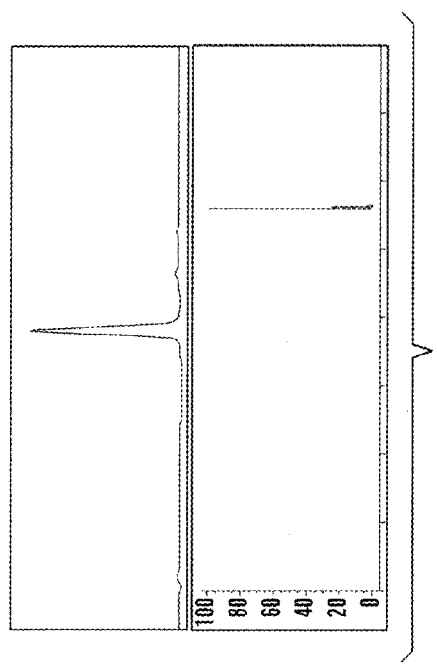
FIG. 6A shows the structure and the images of the solution with and without UV irradiation.
Figure 6A:
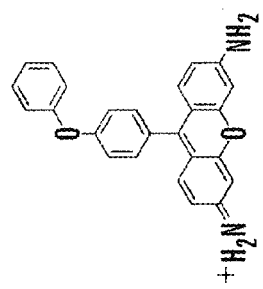
Figure 6B:
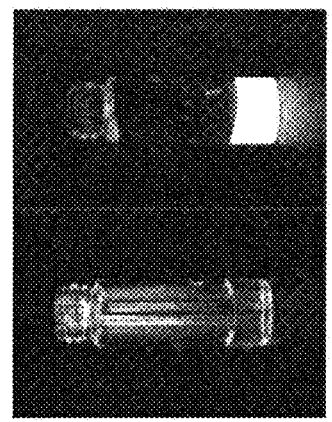
FIG. 6B shows the LCMS trace in 250 nm and mass spectrum with a value of 379.4 found (calculated: 379.14).
Figure 6C:
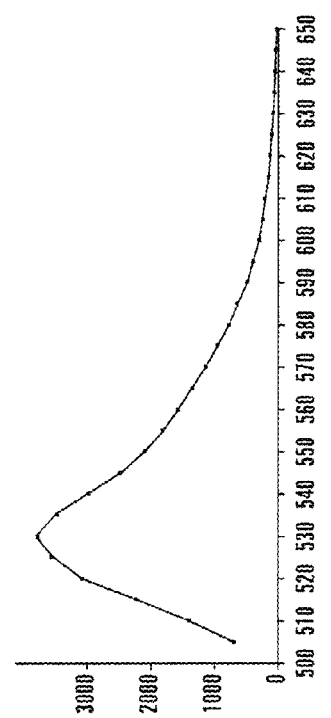
FIG. 6C shows the absorbance spectrum with a $\lambda_{max}$ of 500 nm.
Figure 6D:
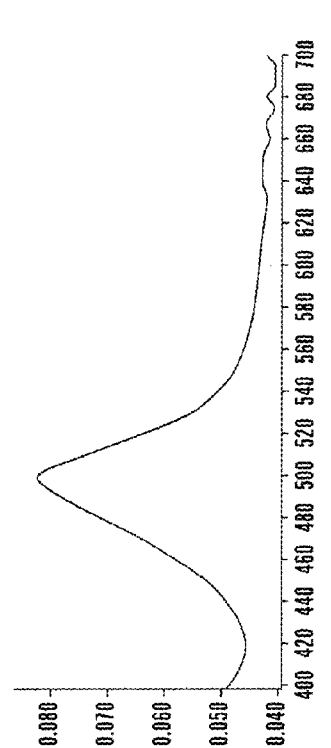
FIG. 6D shows the fluorescence emission spectrum with a $\lambda_{max}$ of 530 nm, excitation 480 nm.
Figure 7A:
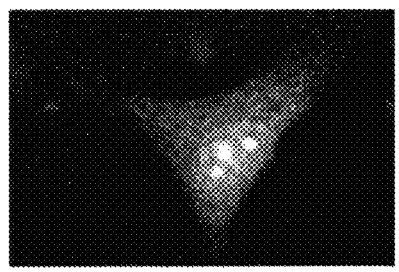
FIGS. 7A-F show the different localization of rosamine molecules (nucleoli, nucleus, lysosome, mitochondria, vesicle, and cytoplasm: B28, B21, L14, A4, J7, and J9 in Table 1).
Figure 7B:
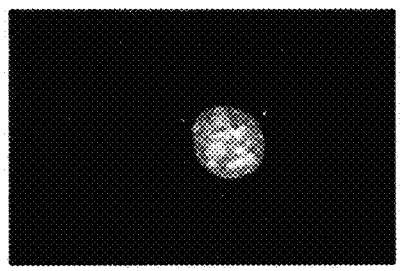
Figure 7C:
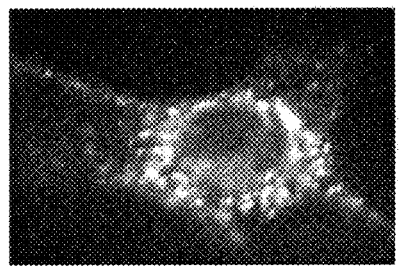
Figure 7D:
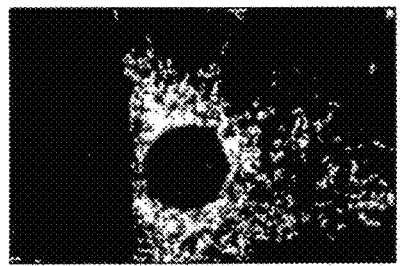
Figure 7E:
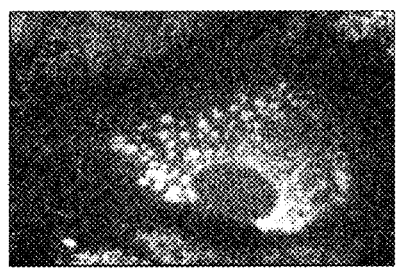
Figure 7F:
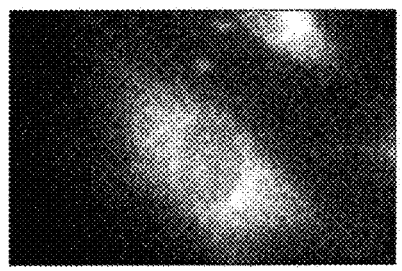
Figure 8:
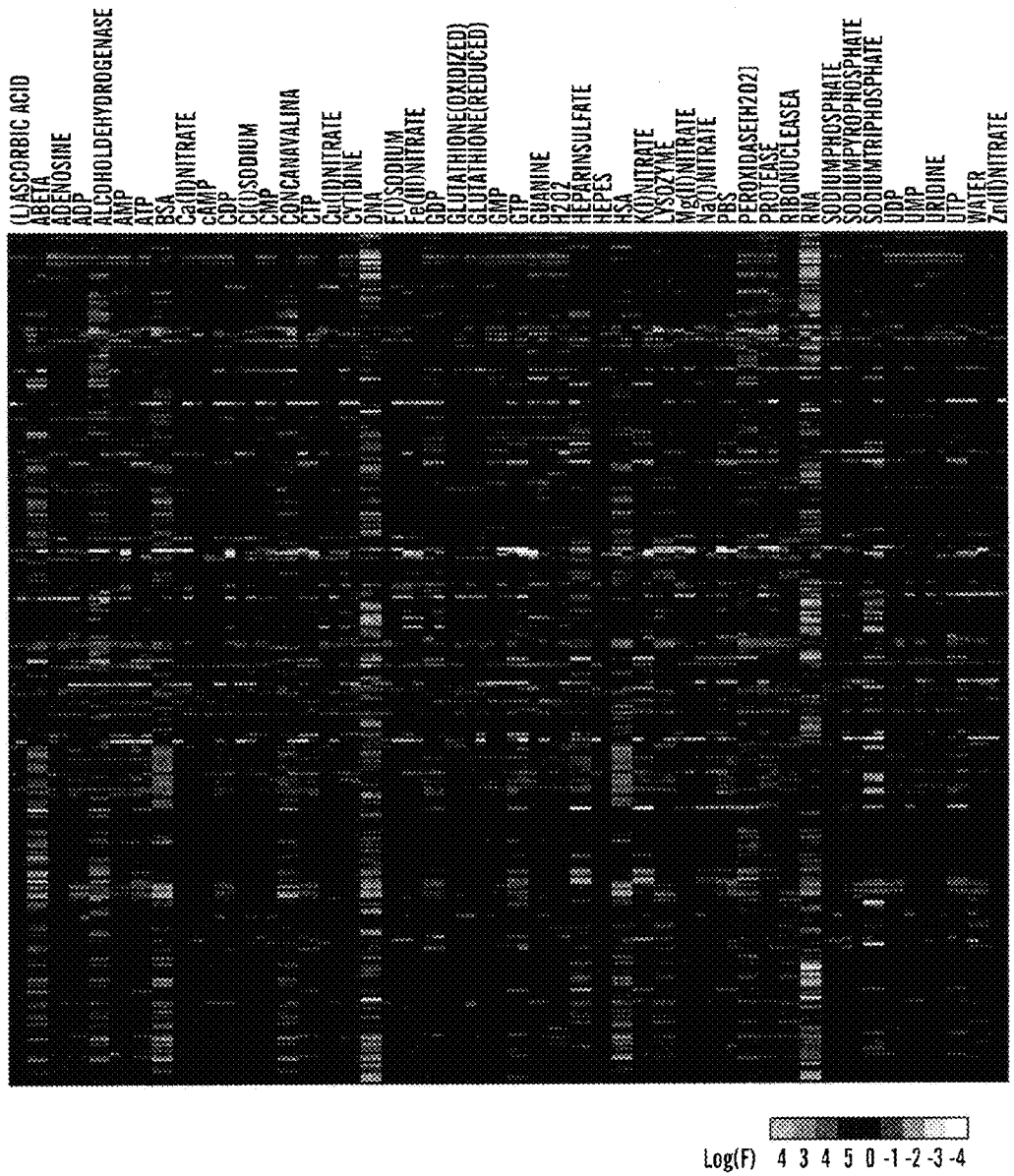
FIG. 8 shows the screening of 240 rosamine libraries with 47 analytes. Lof(F) is a logarithm value of fluorescence intensity change upon addition of the analyte. y-axis: each rosamine molecule, and x-axis: each analyte.
Figure 9:
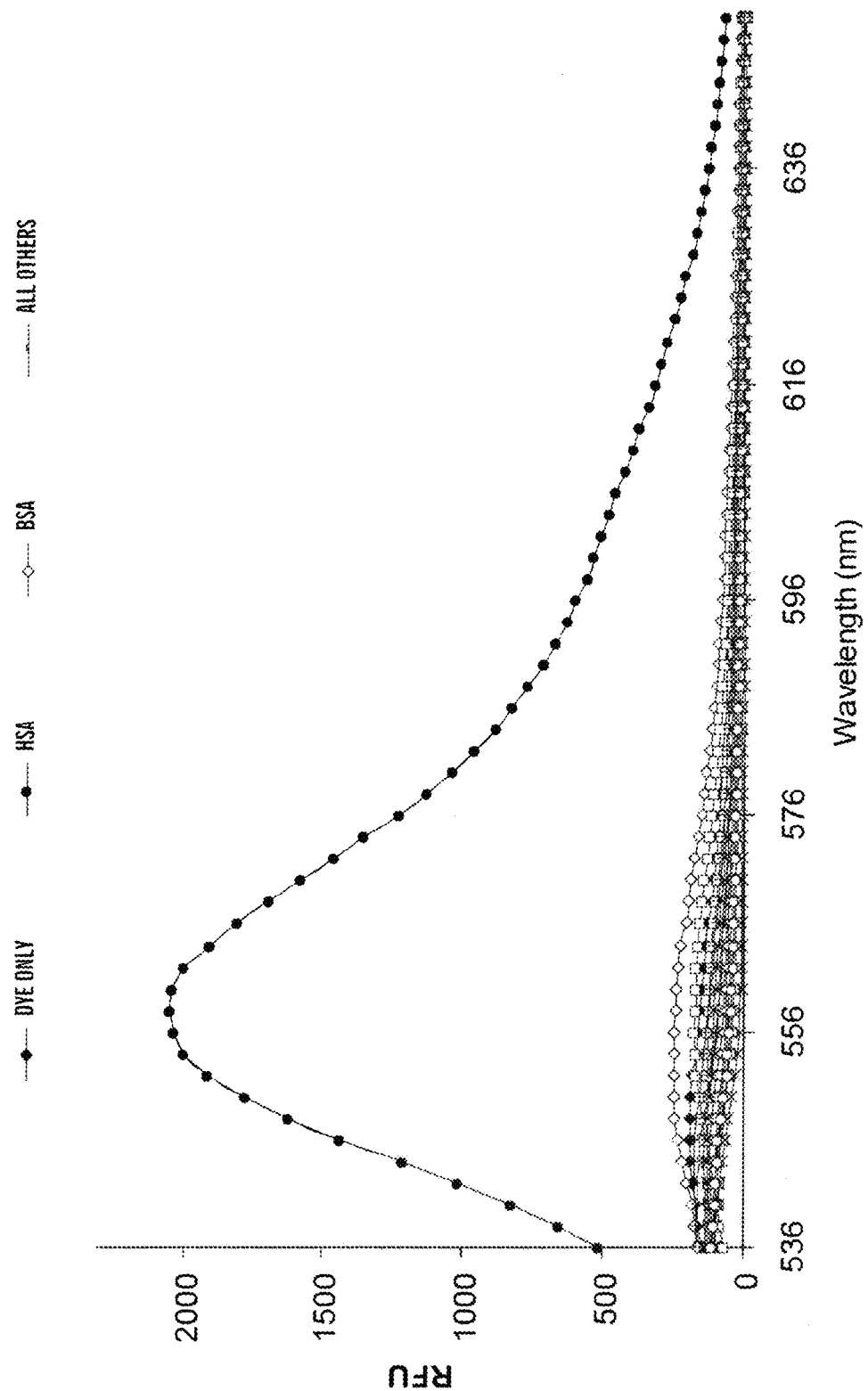
FIG. 9 shows the fluorescence emission response of G13 in Table 1 in the presence of 13 different proteins: control, HSA, BSA, dsDNA, RNA, peroxidase, cellulase A, protease A, lipase, lysozyme, papain, heparin, hemoglobin, and hemicellulase). G13 (10 μM) and all proteins (0.5 mg/mL) in HEPES (10 mM, pH=7.4) show a 12.5 fold change with HSA in 556 nm.

The present invention relates to a method of detecting, in a sample, a cell type of interest and one or more differentiated forms of the cell type of interest. This method includes providing a sample potentially containing a cell type of interest and one or more differentiated forms of the cell type of interest and providing a rosamine derivative compound of the formula:

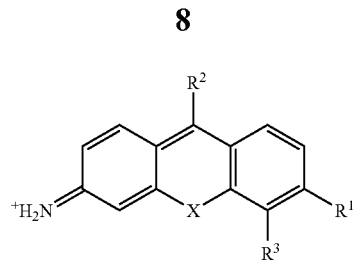

wherein:
X is O, $NR^4$, or S;
$R_1$ is $NR^4R^5$, OH, $NR^4R^6$, or

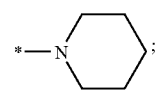

$R^2$ is substituted or unsubstituted phenyl, napthyl,

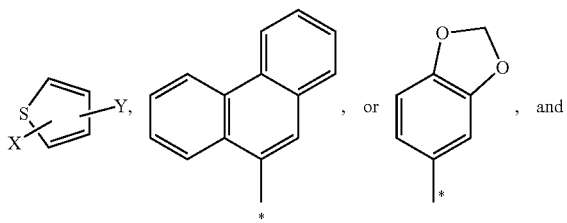

wherein the substituted form of $R^2$ has one or more substituents independently selected from the group consisting of halogen, $NR^4R^5$, $OR^7$, $SR^4$, aryl, $C_1$ to $C_6$ alkyl,

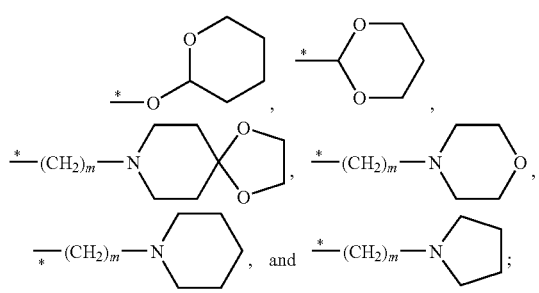

$R^3$ is H or with $R^1$ collectively forms a fused ring of the structure of

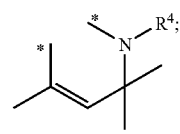

$R^4$ is H or $C_1$ to $C_6$ alkyl;
$R^5$ is H, $C_1$ to $C_6$ alkyl, or with $R^4$ collectively forms a ring structure;
$R^6$ is $(CH_2)_n NR^4R^8$;
$R^7$ is H, $C_1$ to $C_6$ alkyl, or aryl;
$R^8$ is H or $C_1$ to $C_6$ alkyl;
Y is alkyl or halogen;

n is 1 to 3;
m is 0 to 3; and
* is a site on a substituent which binds to the rosamine derivative compound, where the rosamine compound produces differing fluorescent signals for the cell type of interest than for the one or more differentiated forms of the cell type of interest. The sample is with the rosamine derivative compound under conditions effective to produce differing fluorescent signals for the cell type of interest than for the one or more differentiated forms of the cell type of interest, if present in the sample. The presence of the cell type of interest and the one or more differentiated forms of the cell type of interest is detected based on fluorescent signals emitted by the sample following the contacting step.

Another aspect of the present invention relates to a method of screening for compounds which inhibit differentiation of a cell type of interest to one or more differentiated forms of the cell type of interest. This method includes providing a sample containing a cell type of interest and providing a rosamine derivative compound of the formula:

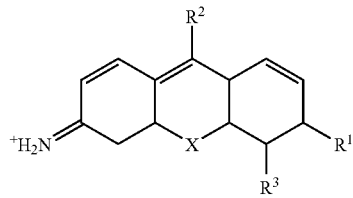

wherein:
X is O, NR$^4$, or S;
R$_1$ is NR$^4$R$^5$, OH, NR$^4$R$^6$, or

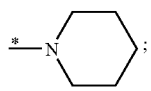

R$^2$ is substituted or unsubstituted phenyl, napthyl,

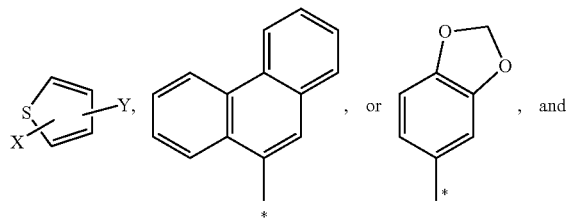

wherein the substituted form of R$^2$ has one or more substituents independently selected from the group consisting of halogen, NR$^4$R$^5$, OR$^7$, SR$^4$, aryl, C$_1$ to C$_6$ alkyl,

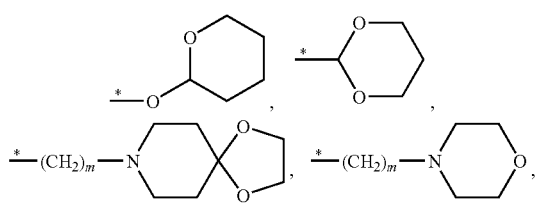

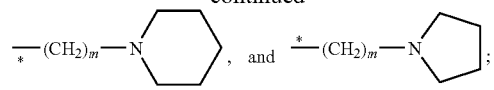

R$^3$ is H or with R$^1$ collectively forms a fused ring of the structure of

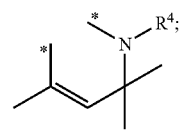

R$^4$ is H or C$_1$ to C$_6$ alkyl;
R$^5$ is H, C$_1$ to C$_6$ alkyl, or with R$^4$ collectively forms a ring structure;
R$^6$ is (CH$_2$)$_n$NR$^4$R$^8$;
R$^7$ is H, C$_1$ to C$_6$ alkyl, or aryl;
R$^8$ is H or C$_1$ to C$_6$ alkyl;
Y is alkyl or halogen;
n is 1 to 3;
m is 0 to 3; and
* is a site on a substituent which binds to the rosamine derivative compound, where the rosamine compound produces differing fluorescent signals for the cell type of interest than for the one or more differentiated forms of the cell type of interest. A candidate compound is also provided and the sample, the candidate compound, and the rosamine derivative compound are then contacted. The sample, prior to after said contacting, is subjected to conditions effective to cause the cell type of interest in the sample to undergo differentiation to the one or more differentiated forms of the cell type of interest. Candidate compounds which reduce fluorescent signal for differentiated forms of the cell type of interest are identified as having potential activity as inhibitors of differentiation of the cell type of interest.

Most rhodamine derivatives including rosamine (rhodamine derivative without 2'-carboxylic acid) (Jiao et al., "Microwave-Assisted Syntheses of Regioisomerically Pure Bromorhodamine Derivatives," *Organic Lett* 5:3675-3677 (2003), which is hereby incorporated by reference in its entirety), have been prepared by individual condensation reaction under a strong acidic condition, (U.S. Pat. No. 5,686,261, to Zhang; Liu et al., "Rational Design and Synthesis of a Novel Class of Highly Fluorescent Rhodamine Dyes that Have Strong Absorption at Long Wavelengths," *Tetrahedron Lett* 44:4355-4359 (2003); Jiao et al., "Microwave-Assisted Syntheses of Regioisomerically Pure Bromorhodamine Derivatives," *Organic Lett* 5:3675-3677 (2003); Han et al., "Microwave-Assisted Functionalization of Bromo-Fluorescein and Bromorhodamine Derivatives," *Tetrahedron Lett* 44:9359-9362 (2003); and Felton et al., "Chromatographically Pure Fluorescein and Tetramethylrhodamine Isothiocyanates," *Anal Biochem* 2:178-180 (1961), which are hereby incorporated in their entirety), requiring difficult or tedious purification, which is a serious bottleneck for library generation. Thus, to incorporate solid phase chemistry to generate the final product has been examined, circumventing acidic reflux condition and time-consuming purification steps. In particular, a rosamine structure was chosen to introduce the flexibility since the rotation of 9-phenyl ring without a 2'-substituent was suspected to induce the fluorescence change on the similar xanthene structure (Urano et al., "Evolution of Fluorescein as a Platform for Finely Tunable Fluorescence Probes," *J Am Chem Soc* 127:4888-4894 (2005), which is hereby incorporated in its entirety).

As shown in Table 1, two diversities ($T^1$ and $T^2$) were introduced successively, and one amino-functionality of the xanthene core was used as a linker to the resin (Scheme 1). Initially, three different 3-amino-6-nitro-9H-xanthone derivatives (S3, Y=O, NH, S) were synthesized that allowed the selective modification on the 3-amino position, and the 6-nitro group was utilized as a linker after reduction to amino group. Therefore, twelve different unsymmetrical xanthone derivatives (S5, $T^1$ building blocks, A-L in Table 1) containing different sizes and functionalities in addition to oxygen, sulfur, and nitrogen bridges were synthesized. Each intermediate was loaded on the 2-chlorotrityl chloride resin (S6) and heated with 33 different Grignard reagents for 2-4 days for the second diversity ($T^2$ building block in Table 1) ($T^1$ building block (D) proceeded t-butyldimethylsilyl group protection after loading on the resin, then Grignard reaction. Among $T^2$ building blocks, acetal protecting groups of 5 and 21 were removed after the Grignard reaction). The successive acidic cleavage (1% TFA in dichloromethane) from the resin resulted in the dehydration, giving the fully conjugated rosamine derivatives. All compounds in the library were characterized by HPLC-MS for the identification and purity (average purity is 93% at 250 nm, See FIGS. 1-11). 240 compounds have been prepared in this approach, having a relatively wide range of structural and spectral diversities (Excitation ranges from 480-545 nm and emission ranges from 530-605 nm). The quantum yield highly varies from 0.00025 to 0.89 in PBS (10 mM). Modification on $T^1$ was changing the excitation and emission maximum wavelength as well as fluorescence intensity while the modification on $T^2$ was slightly changing the excitation and emission maximum wavelength, but largely changing fluorescence intensity depending on the substituents.

As used above, and throughout the description of the present invention, the following terms, unless otherwise indicated, shall be understood to have the following meanings:

The term "alkyl" means an aliphatic hydrocarbon group which may be straight or branched having about 1 to about 6 carbon atoms in the chain. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, and 3-pentyl.

The term "aryl" means an aromatic monocyclic or multicyclic ring system of 6 to about 14 carbon atoms, preferably of 6 to about 10 carbon atoms. Representative aryl groups include phenyl and naphthyl.

The term "halogen" means fluoro, chloro, bromo, or iodo.

The term "substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is keto (i.e., =O), then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The fluorescent library is based on a rosamine scaffold including rosamine, thio-rosamine, and acridine structures, and the synthetic scheme is in Scheme 1.

TABLE 1

$T^1$ Building Block (S5):

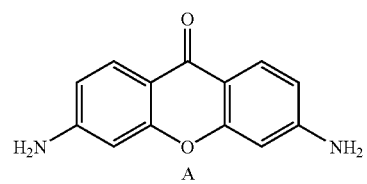 [SMILES: Nc1ccc2c(=O)c3ccc(N)cc3oc2c1]

A

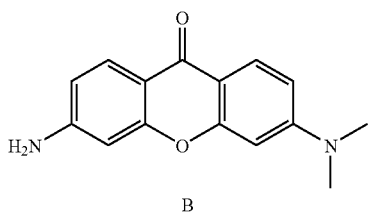

B

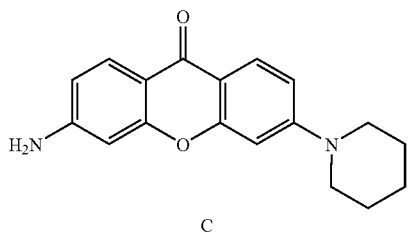

C

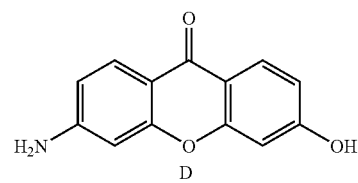

D

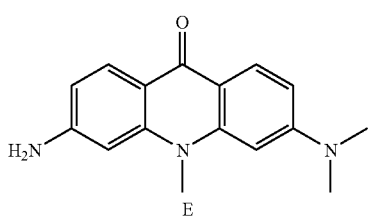 [SMILES: CN(C)c1ccc2c(=O)c3ccc(N)cc3n(C)c2c1]

E

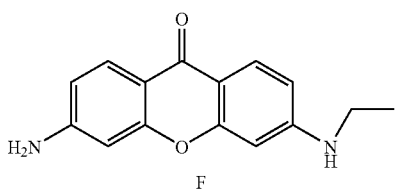

F

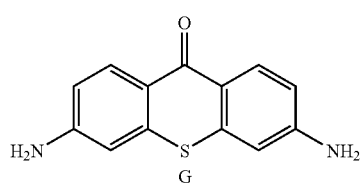 [SMILES: Nc1ccc2c(=O)c3ccc(N)cc3sc2c1]

G

TABLE 1-continued
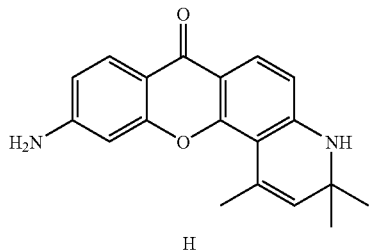
H
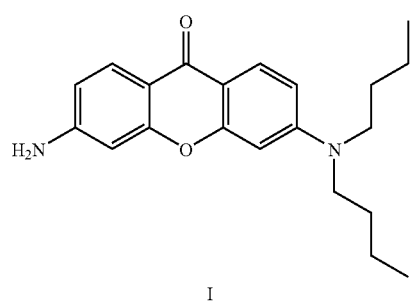
I
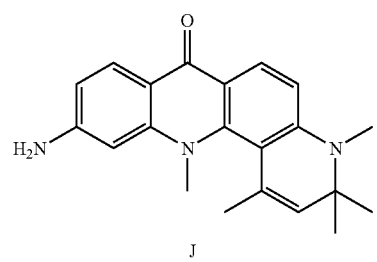 [SMILES: CC1=CC(C)(C)N(C)c2ccc3c(=O)c4ccc(N)cc4n(C)c3c21]
J
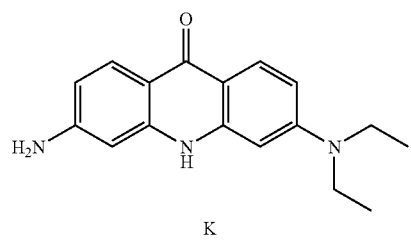
K
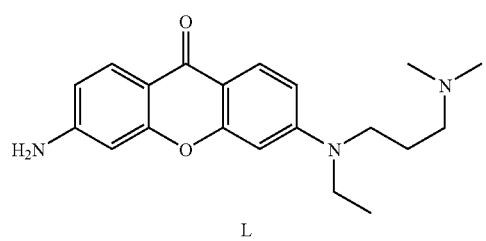 [SMILES: CCN(CCCN(C)C)c1ccc2c(=O)c3ccc(N)cc3oc2c1]
L
TABLE 1-continued
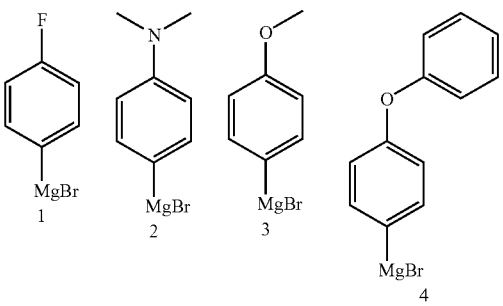
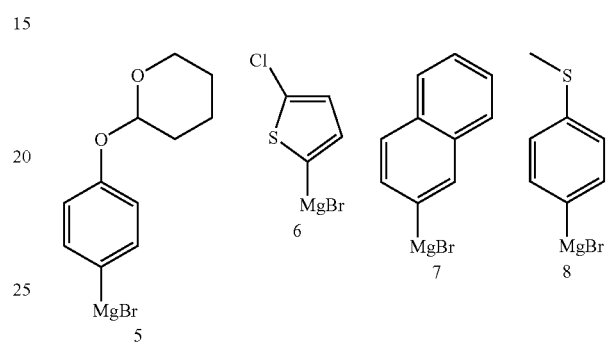
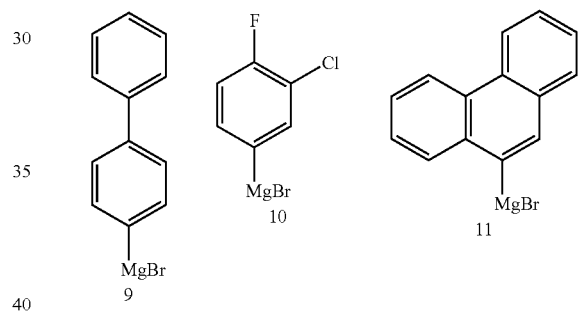
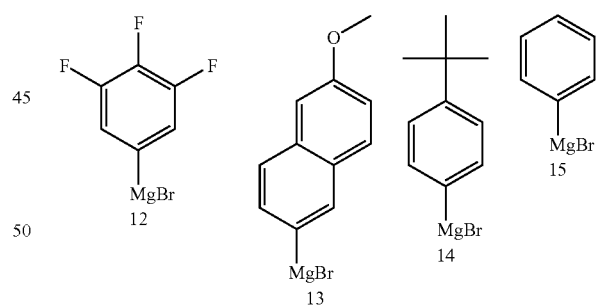
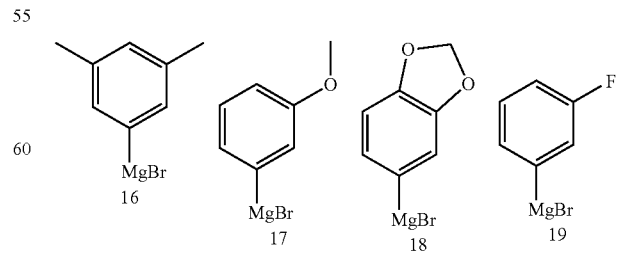
$T^2$ Building Block:

TABLE 1-continued

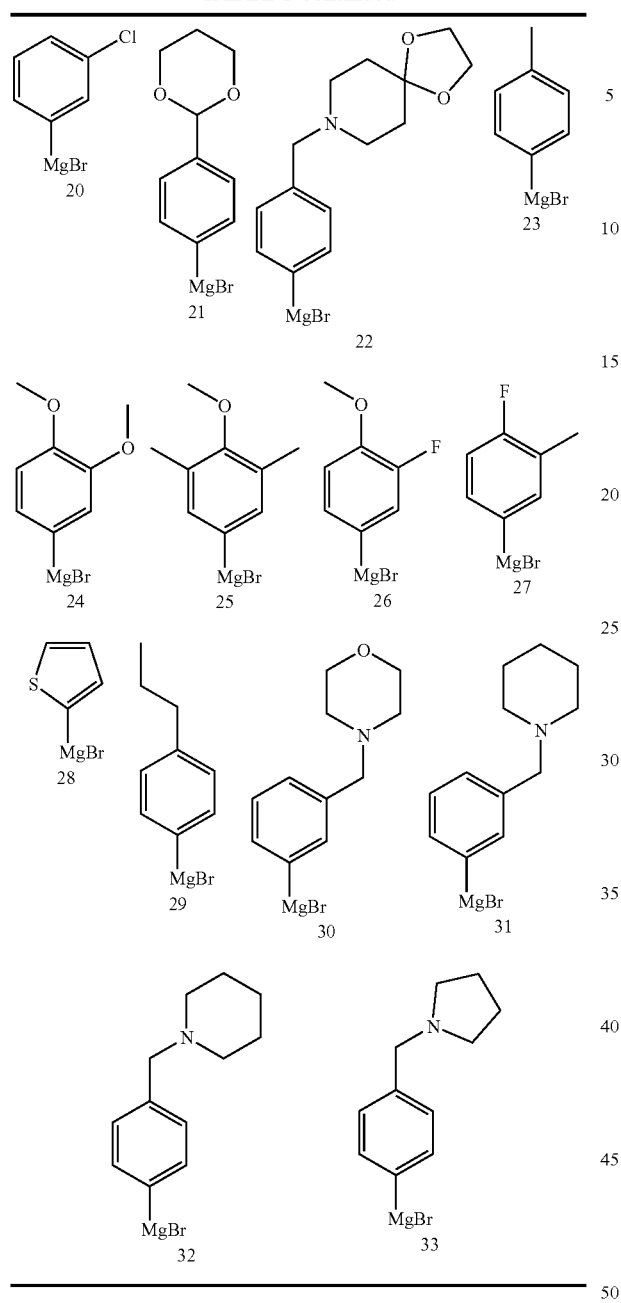

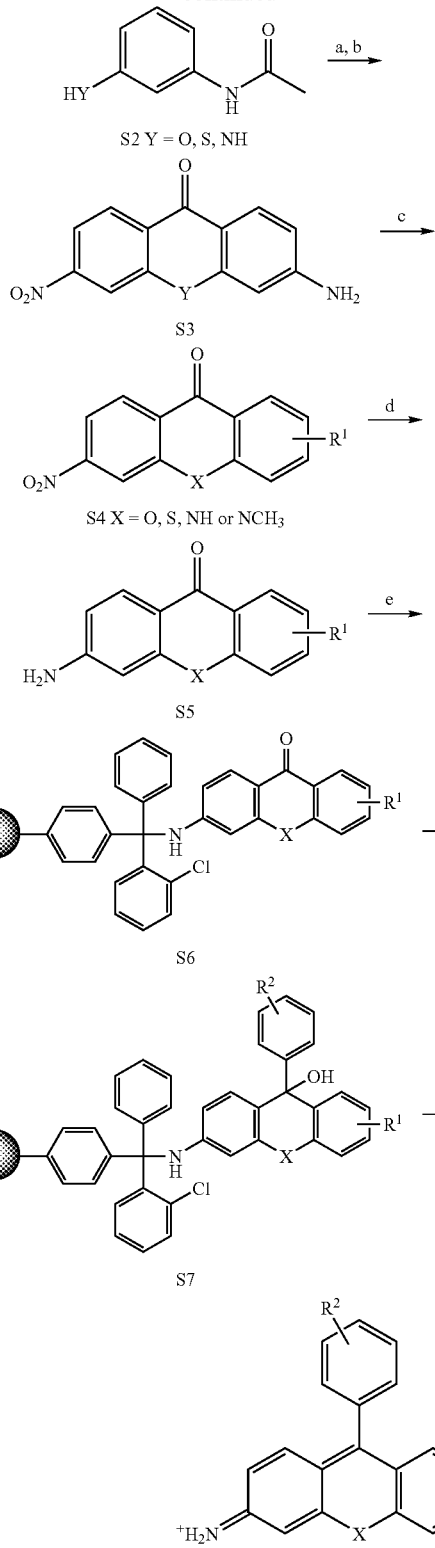

Scheme 1 Synthesis generating rosamine-like library and building blocks; a) K$_2$CO$_3$, Cu, DMF, 130° C.; b) H$_2$SO$_4$, 80° C.; c) modification for T$^1$ (see the section "Synthesis of all the intermediate" for each reaction); d) SnCl$_2$, EtOH, 90° C.; e) 3-chloro-trityl chloride resin, pyr, CH$_2$Cl$_2$/DMF; f) R$^2$ Grignard reagent, THF; g) 1% TFA, CH$_2$Cl$_2$

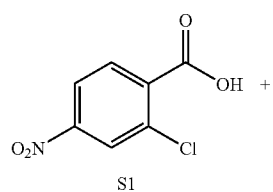

Different cell lines can be utilized, including human normal and cancer cells, muscle cells, and embryonic cells to investigate any potential phenotype when treated with rosamine derivative compounds. A particular phenotype may be monitored through a confocal microscope or distinct fluorescence changes. The lead compound is attached to agarose or modified with a chemical or photoaffinity tag for isolation and identification of the target protein. The cell type of interest and the one or more differentiated forms of the cell type of interest, respectively, can be myoblasts and myotubes; neural stem cells and neurons, astrocytes, oligodendrocytes; mesenchymal stem cells and osteoblasts, chondrocytes, myocytes, adipocytes; and endocrine progenitor cells and pancreatic cell types, including alpha and beta cells.

This procedure can be carried out, for example, by growing HeLa and 3T3 cells on the glass bottom of 96-well black plates. Each rosamine derivative compound is added to the cell culture well at the desired concentration. An optical fluorescence microscope with a 100× oil immersion objective is used for the imaging experiment to detect the localization or the specific position of each compound in the cell.

Library based development of new optical imaging probes with optimized properties may be applied for single-molecule resolution optical imaging in living cells. The present invention utilizes libraries of rosamine-type fluorophores for this purpose.

EXAMPLES

The following examples are provided to illustrate embodiments of the present invention but are by no means intended to limit its scope.

Examples 1-15

Synthesis of all the Intermediates

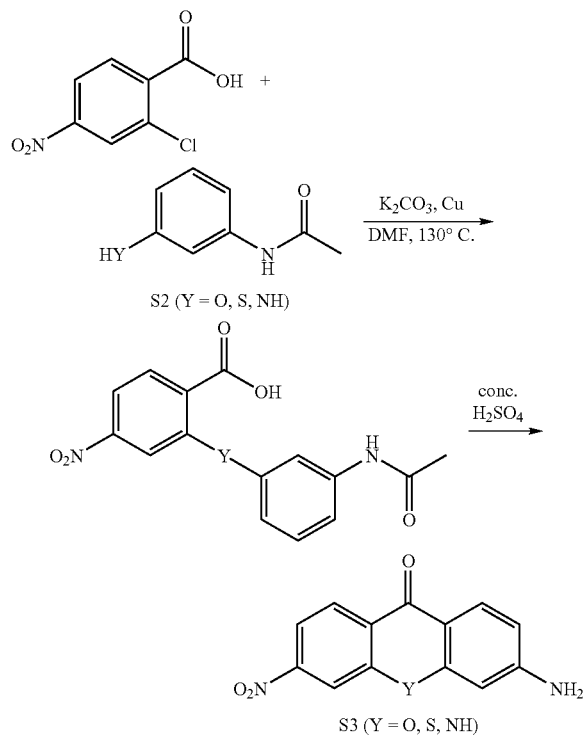

Example 1

Synthesis of 3-Amino-6-Nitro-9H-Xanthone (S3, Y=O)

To a solution of 2-chloro-4-nitrobenzoic acid (3 g, 14.88 mmol) in DMF (40 mL) was added 3-3'-acetamidolphenol (2.47 g, 16.38 mmol), potassium carbonate (3.08 g, 16.38 mmol), and copper powder (102 mg, 1.61 mmol). After heating at 130° C. overnight, the reaction mixture was cooled to room temperature and poured to ice-1 N HCl solution (300 mL) slowly. The solution was stirred until the brown solid was formed. The solid was filtered off and washed with cold water to yield a brown solid (3.1 g). A crude solid was dissolved in conc. sulfuric acid (20 mL) and heated at 80° C. for 1 hour. After cooling to room temperature, the reaction mixture was poured to ice (350 mL volume) and stirred for 1 hour. The precipitated solid was filtered off and re-suspended in 2.5% aq. sodium carbonate solution. The solid was filtered and washed with cold water and dried under vacuum. The solid was further recrystallized in pyridine or pyridine/water to yield 1.23 g of S3 (Y=O) (60%, two steps) as a yellowish-brown solid. $^1$H-NMR (DMSO-d6) δ 8.37 (d, J=2.0, 1H), 8.32 (d, J=8.4, 1H), 8.15 (dd, J=2.0, 8.4, 1H), 7.88 (d, J=8.8, 1H), 6.75 (bs, 2H), 6.72 (dd, J=2.0, 8.8, 1H), 6.56 (d, J=2.0, 1H). ESI-MS m/z (H+H) calc'd: 257.2, found 257.1.

Example 2

Synthesis of 3-Amino-6-nitro-10H-acridin-9-one (S3, Y=NH)

The compound S3 (Y=NH) was prepared using 2-chloro-4-nitrobenzoic acid and 3'-aminoacetanilide in the same way as S3 (Y=O). $^1$H-NMR (DMSO-d6) δ 11.54 (s, 1H), 8.32 (d, J=8.8, 1H), 8.26 (d, J=2.0, 1H), 7.92 (d, J=8.8, 1H), 7.86 (d, J=2.0, 8.4, 1H), 6.60 (dd, J=2.0, 8.8, 1H), 6.43 (d, J=2.0, 1H), 6.36 (bs, 2H). ESI-MS m/z (M+H) calc'd: 256.1, found 256.1.

Example 3

Synthesis of 3-Amino-6-nitro-thioxanthen-9-one (S3, Y=S)

3'-acetamidothiophenol (S2, Y=S) was prepared from 3'-aminothiophenol and acidic anhydride in ethyl acetate. To a solution of 3'-aminothiophenol (1.0 mL, 9.42 mmol) in ethyl acetate (50 mL) was added acidic anhydride (10.40 mmol) at 0° C., and slowly warmed up to room temperature while stirring for 1 hr. The reaction mixture was diluted with ethyl acetate and washed with 1N HCl and brine solution. The organic layer was dried over sodium sulfate, and the filtrate was concentrated and purified by silica column chromatography (ethyl acetate/hexane=1/1) (1.34 g, 85%), which was used for preparation of S3 (Y=S) in the same way as S3 (Y=O). The resulting solid S3 (Y=S) was purified by silica gel column chromatography (ethanol/methylene chloride) to give a brownish solid (25%). $^1$H-NMR (CDCl$_3$+CD$_3$OD) δ 8.69 (d, J=8.8, 1H), 8.45 (d, J=2.4, 1H), 8.34 (d, J=8.8, 1H), 8.19 (dd, J=2.4, 8.8, 1H), 6.84 (dd, J=2.4, 8.8, 1H), 6.72 (d, J=2.0, 1H). ESI-MS m/z (M+H) calc'd: 273.0, found 273.2.

Example 4

Synthesis of A (3-Amino-6-amino-xanthen-9-one)

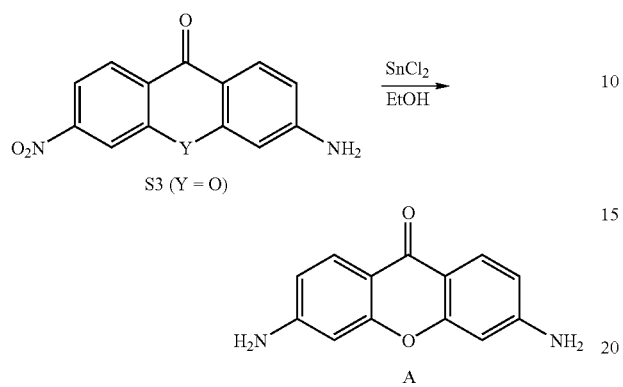

To a solution of S3 (540 mg, 2.11 mmol) dissolved in ethanol (50 mL) tin chloride dihydrate was added (1.90 g, 8.44 mmol) and refluxed overnight. After completed, the reaction mixture was concentrated and solidified by adding aq. 1N-NaOH solution. The solid was filtered and washed with water, and recrystallized from aqueous pyridine to give the compound A (219 mg, 45.8%). $^1$H-NMR (CDCl$_3$+CD$_3$OD) δ 7.98 (d, J=8.8, 2H), 6.65 (dd, J=2.4, 8.8, 2H), 6.60 (d, J=2.4, 2H). ESI-MS m/z (M+H) calc'd: 227.1, found 227.2$^+$.

Example 5

Synthesis of B (3-Amino-6-dimethylamino-xanthen-9-one)

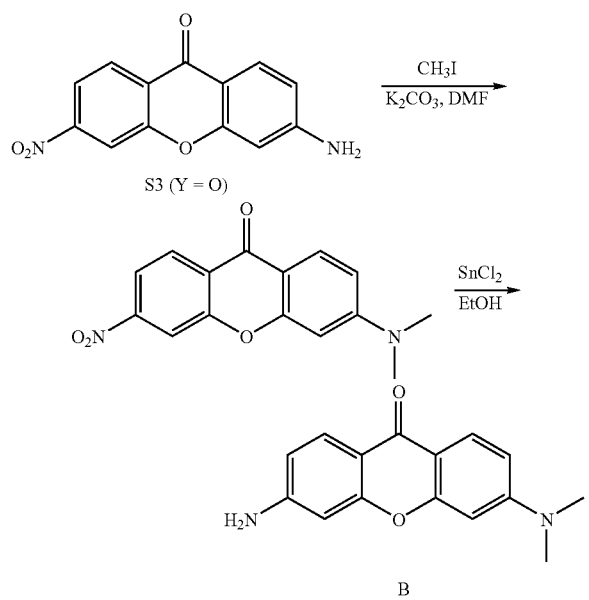

To a solution of S3 (1.2 g, 4.68 mmol) in DMF (40 mL) was added potassium carbonate (1.6 g, 11.57 mmol) and iodomethane (1.7 mL, 27.3 mmol). After heating at 100° C. for 2 days, the mixture was cooled to room temperature, and diluted with dichloromethane and washed with aq. 1N HCl, aq. NaHCO$_3$ and brine solution. The organic layer was dried over sodium sulfate, and the filtrate was concentrated and solidified in EA/Hexane (660 mg). To a crude compound in ethanol (50 mL) was added tin chloride dihydrate (2.09 g, 9.27 mmol). After refluxing overnight, the solution was concentrated completely and solidified in aq. 1N NaOH solution. The solid was filtered and washed with water, and purified by silica gel column chromatography to give an orange solid (400 mg, 33.6%, two steps). $^1$H-NHR(CDCl$_3$) δ 8.13 (d, J=8.8, 1H), 8.10 (d, J=8.8, 1H), 6.70 (dd, J=2.4, 8.8, 1H), 6.61 (dd, J=2.0, 8.4, 1H), 6.53 (d, J=2.4, 1H), 6.47 (d, J=2.8, 1H), 4.20 (bs, 2H), 3.10 (s, 6H). ESI-MS m/z (M+H) calc'd: 255.1, found 255.2$^+$.

Example 6

Synthesis of C (3-Amino-6-piperidin-1-yl-xanthen-9-one)

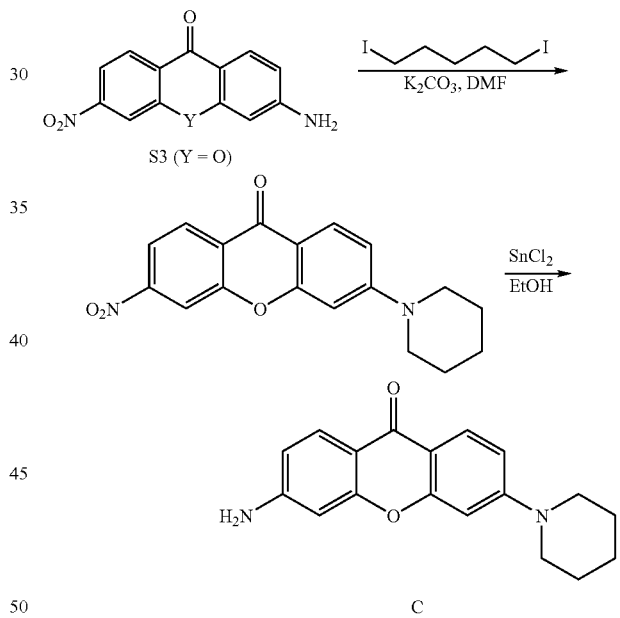

To a solution of S3 (1.08 g, 4.22 mmol) in DMF (40 mL) was added potassium carbonate and 1,5-diiodopentane (3.2 mL, 21.5 mmol). After heating at 100° C. until completed, the reaction mixture was cooled to room temperature and diluted with dichloromethane, and washed with aq. 1N HCl, aq. NaHCO$_3$, and brine solution. The organic layer was dried over sodium sulfate, and the filtrate was concentrated and purified by silica gel column chromatography (methanol/MC=1:80) to give a deep organge solid (620 mg). To the solid in ethanol (50 mL) tin chloride dihydrate (1.28 g, 5.67 mmol) was added and refluxed overnight. After completion, the reaction mixture was concentrated and purified by silica gel column chromatography (ethanol/MC=1:50) to give a product C (200 mg, 16.2%, two steps). $^1$H-NHR(CDCl3) δ 8.03 (d, J=8.8, 1H), 7.98 (d, J=8.4, 1H), 6.87 (dd, J=2.0, 8.8, 1H), 6.65

(d, J=2.4, 1H), 6.63 (dd, J=2.0, 8.8, 1H), 6.53 (d, J=2.0, 1H), 4.33 (s, 2H), 3.37 (bs, 4H), 1.68 (bs, 6H). ESI-MS m/z (M+H) calc'd: 295.1, found 295.0⁺.

Example 7

Synthesis of Compound D
(3-Amino-6-hydroxy-xanthen-9-one)

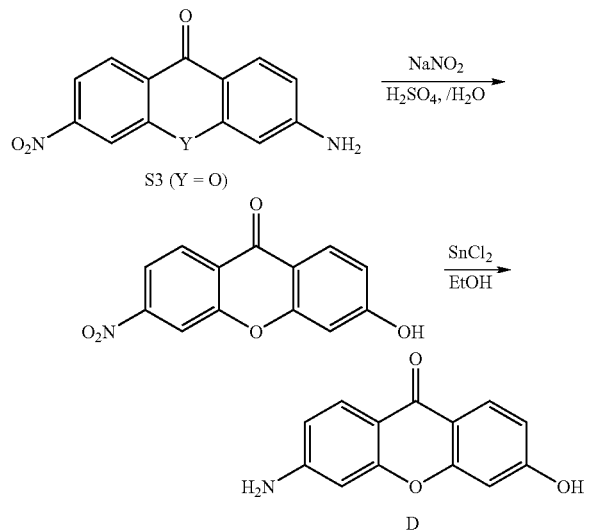

To a solution of S3 (600 mg, 2.34 mmol) in concentrated sulfuric acid and water (5 mL/5 mL) was added dropwise a solution of sodium nitrite (480 mg, 6.96 mmol) in water (1 mL) at 0° C. The reaction mixture was slowly warmed to room temperature while stirring for 1.5 hr and poured into boiling water (20 mL). After stirring at 95° C. for 30 min, the solution was cooled to room temperature. The precipitate was filtered and washed with cold water to yield the solid. A crude solid was refluxed overnight with tin chloride dihydrate (2.11 g, 9.36 mmol) in ethanol (50 mL). The reaction mixture was concentrated and solidified by adding aq. NaHCO₃ solution. The solid was filtered and washed with cold water, and purified by silica gel column chromatography to yield D (160 mg, 30%, two steps) as a yellow solid. ¹H-NMR (CDCl₃+CD₃OD) δ 8.08 (d, J=8.8, 1H), 7.99 (d, J=8.4, 1H), 6.84 (dd, J=2.4, 8.8, 1H), 6.80 (d, J=2.0, 1H), 6.68 (dd, J=2.4, 8.8, 1H), 6.58 (d, J=2.0, 1H). ESI-MS m/z (M+H) calc'd: 228.1, found 228.0⁺.

Example 8

Synthesis of 3-Amino-6-dimethylamino-10-methyl-10H-acridin-9-one (E)

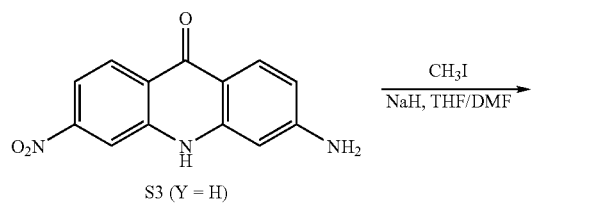

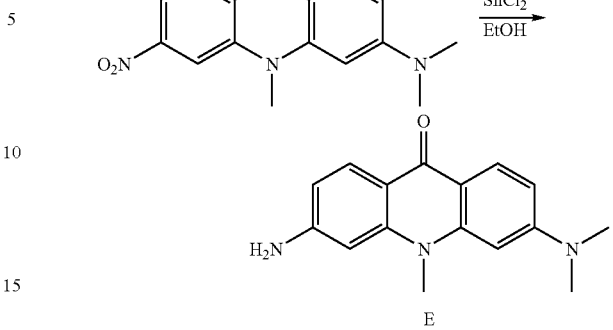

To a solution of S3 (2.0 g, 7.55 mmol) in DMF/THF (6.6 mL/80 mL) was added sodium hydride (906 mg, 37.7 mmol) at 0° C. After stirring for 10 min, iodomethane (1.88 mL, 30.2 mmol) was added and stirred overnight. Ethyl acetate was added to the reaction mixture, and the resulting precipitate was filtered. The solid was purified by silica gel column chromatography (methanol/MC=1:50) to give a brown solid (450 mg). To a solid in ethanol (50 mL) tin chloride dihydrate (1.38 g, 6.14 mmol) was added and refluxed overnight. After completion, the reaction mixture was concentrated and solidified by adding 1N aq. NaOH solution. The solid was filtered and washed with water, and purified by column chromatography, yielding E (400 mg, 20.0%, two steps). ¹H-NMR (CDCl₃+CD₃OD) δ 8.27 (d, J=9.2, 1H), 8.21 (d, J=8.4, 1H), 6.78 (dd, J=2.4, 9.2, 1H), 6.69 (d, J=2.0, 1H), 6.66 (dd, J=1.6, 8.4, 1H), 6.44 (d, J=2.0, 1H), 3.81 (s, 3H), 3.18 (s, 6H). ESI-MS m/z (M+H) calc'd: 268.1, found 268.2⁺.

Example 9

Synthesis of 3-Amino-6-ethylamino-xanthen-9-one (F)

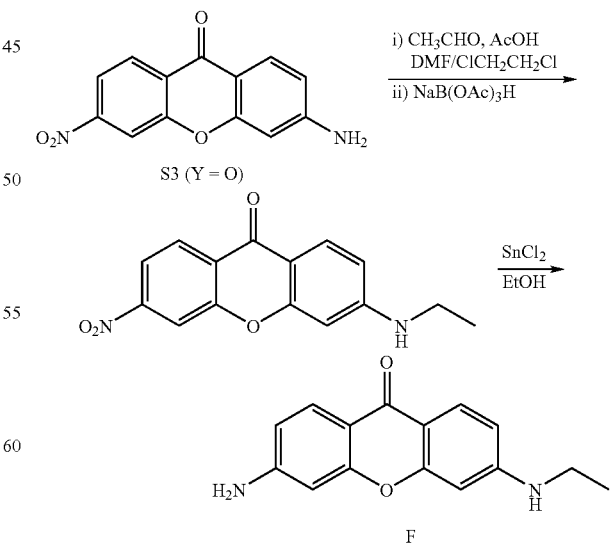

To a solution of S3 (1.0 g, 3.90 mmol) in DMF (5 mL) and 1,2-dichloroethane (20 mL) were added acetaldehyde (0.438 mL, 7.80 mmol) and acetic acid (1.4 mL). After stirring for 1 hr, sodium triacetoxyborohydride (2.48 g, 11.7 mmol) was added and stirred overnight. The reaction mixture was diluted with dichloromethane and then washed with aq. NaHCO$_3$ and brine solution. The organic layer was dried over sodium sulfate and concentrated, and column chromatographed on silica gel (ethanol/dichloromethane=1/100) to yield a deep orange solid (667 mg, 60%). $^1$H-NMR (DMSO-d6) δ 8.34 (d, J=2.4, 1H), 8.32 (d, J=8.8, 1H), 8.16 (dd, J=2.0, 8.8, 1H), 7.89 (d, J=8.8, 1H), 7.28 (broad t, J=5.2, 1H), 6.76 (dd, J=2.0, 8.8, 1H), 6.51 (d, J=2.0, 1H), 3.22 (m, 2H), 1.22 (t, J=7.2, 3H). ESI-MS m/z (M+H) calc'd: 285.1, found 285.0 The solid (660 mg) was refluxed overnight with tin chloride dihydrate (2.11 g, 9.35 mmol) in ethanol (80 mL). The reaction mixture was concentrated and solidified by adding aq. NaOH solution. The filtered solid was purified by silica gel column chromatography (ethanol/dichloromethane) to give compound F as a yellow solid (243 mg, 41%). $^1$H-NMR (CDCl$_3$) δ 8.09 (d, J=8.8, 1H), 8.06 (d, J=8.8, 1H), 6.61 (dd, J=2.0, 8.4, 1H), 6.53 (d, J=2.0, 1H), 6.53 (dd, J=2.4, 8.8, 1H), 6.40 (d, J=2.4, 1H), 4.22 (bs, 1H), 4.19 (bs, 2H), 3.27 (m, 2H), 1.32 (t, J=7.2, 3H). ESI-MS m/z (M+H) calc'd: 255.1, found 255.2$^+$.

Example 10

Synthesis of 3,6-Diamino-thioxanthen-9-one (G)

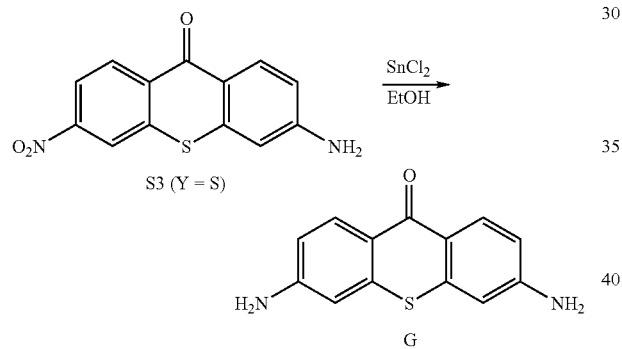

To a solution of S3 (900 mg, 3.31 mmol) in ethanol (125 mL) was added tin chloride (4 g, 17.7 mmol), followed by overnight refluxing. The reaction mixture was concentrated and solidified in aq. 1N NaOH solution. The solid was filtered, dried, and column chromatographed on silica gel (ethanol/dichloromethane), yielding G (250 mg, 32%) as a yellow solid. $^1$H-NMR (CDCl$_3$) δ 8.40 (d, J=8.8, 2H), 6.71 (dd, J=2.0, 8.8, 2H), 6.65 (d, J=2.0, 2H), 4.12 (bs, 4H). ESI-MS m/z (M+H) calc'd: 243.1, found 243.2.

Example 11

Synthesis of H

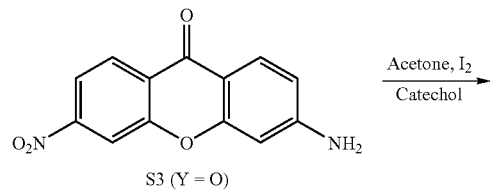

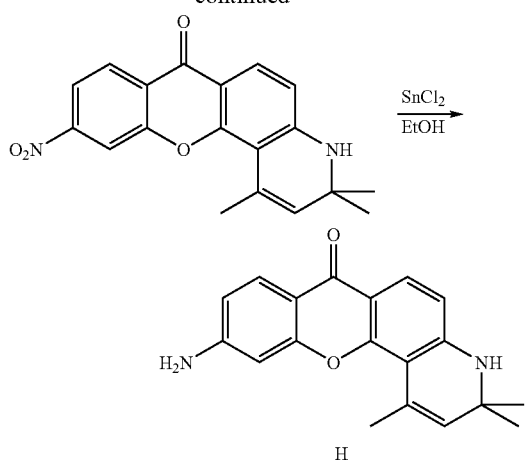

To a solution of S3 (1.2 g, 4.68 mmol) in acetone (150 mL) was added iodine (500 mg, 3.93 mmol) and catechol (600 mg, 5.45 mmol). After refluxing for 2 days, all the solvents were evaporated and the reaction mixture was solidified in methanol and aq. NaHCO$_3$ solution. The solid was filtered and washed with water. The solid was further purified by silica gel column chromatography (ethanol/dichloromethane) giving a solid (800 mg). To the crude solid in ethanol (80 mL) was added tin chloride dihydrate (2.1 g, 2.33 mmol) and refluxed overnight. The reaction mixture was concentrated and solidified in aq. 1N NaOH solution. The filtered solid was purified on silica gel chromatography (ethyl acetate/hexane), yielding H as a solid (260 mg, 18.2%, two steps). $^1$H-NMR (CDCl3) δ 8.07 (d, J=8.4, 1H), 7.98 (d, J=8.4, 1H), 6.61 (dd, J=2.0, 8.4, 1H), 6.53 (d, J=2.4, 1H), 6.44 (d, J=8.8, 1H), 5.29 (s, 1H), 4.34 (bs, 1H), 4.29 (bs, 2H), 2.42 (d, J=1.2, 3H), 1.32 (s, 6H). ESI-MS m/z (M+H) calc'd: 307.1, found 307.2$^+$.

Example 12

Synthesis of 3-Amino-6-dibutylamino-xanthen-9-one (I)

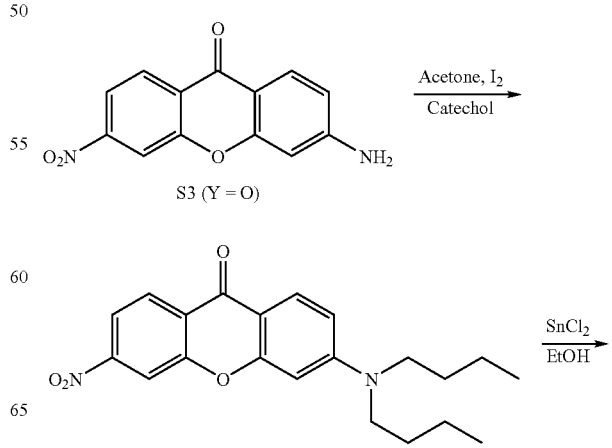

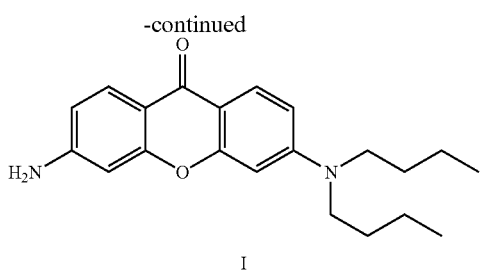

I

To a solution of S3 (500 mg, 1.95 mmol) in THF and DMF (30 mL/10 mL) was added sodium hydride (1 g, 39.6 mmol) and iodobutane (1.8 mL, 15.8 mmol) at 0° C. The solution was then warmed slowly to room temperature and stirred overnight. The solution was diluted with dichloromethane and washed with 1N HCl solution, aq. NaHCO$_3$ solution and brine. The organic layer was dried over sodium sulfate. The filtrate was concentrated and purified by silica gel column chromatography (ethyl acetate/hexane=1/10) to yield the orange solid (250 mg). The solid was refluxed overnight with tin chloride dihydrate (450 mg, 2.0 mmol) in ethanol (50 mL). The reaction mixture was concentrated and solidified in aq. 1N NaOH solution. The filtered solid was purified by silica gel column chromatography (ethyl acetate/hexane=1/2), yielding I as a yellow solid (150 mg, 22.8%). $^1$H-NMR (CDCl$_3$) δ 8.09 (d, J=1.6, 1H), 8.07 (d, J=2.0, 1H), 6.63 (dd, J=2.4, 8.8, 1H), 6.58 (dd, J=2.4, 8.8, 1H), 6.53 (d, J=2.4, 1H), 6.40 (d, J=2.4, 1H), 4.18 (bs, 2H), 3.36 (t, J=7.8, 4H), 1.63 (m, 4H), 1.40 (sextet, J=7.4, 4H), 0.99 (t, J=7.4, 6H). ESI-MS m/z (M+H) calc'd: 339.2, found 339.2$^+$.

Example 13

Synthesis of J

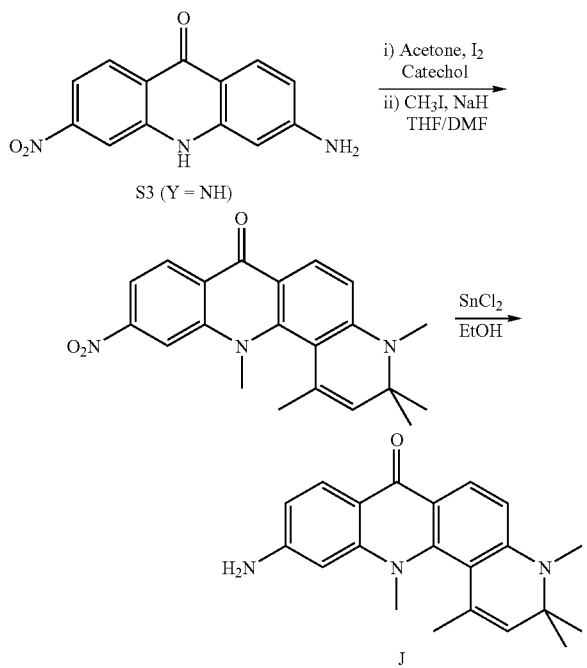

The solution of S3 (3 g, 11.76 mmol), iodine (600 mg, 4.72 mmol), and catechol (600 mg, 5.45 mmol) in acetone (200 mL) was refluxed for 2 days. All the solvents were evaporated, and the reaction mixture was solidified in methanol (40 mL) and aq. NaHCO$_3$ (400 mL). The solid was filtered and washed with water and dried under vacuum. The solid (2.0 g) was dissolved in THF (120 mL) and DMF (20 mL). The sodium hydride (1.15 g, 47.7 mmol) was added at 0° C. After stirring for 10 min, iodomethane (1.86 mL, 29.8 mmol) was added and stirred overnight at room temperature. The reaction mixture was diluted with ethyl acetate and washed with aq. NH$_4$Cl solution, aq. NaHCO$_3$, and brine. The organic layer was dried over sodium sulfate. The filtrate was concentrated and purified by silica gel column chromatography, giving a brown solid (500 mg). The solid was refluxed overnight with tin chloride dihydrate (450 mg, 2.0 mmol) in ethanol (50 mL). The reaction mixture was concentrated and solidified in aq. 1N NaOH solution. The filtered solid was further purified by silica gel column chromatography (ethanol/dichloromethane), yielding J (351 mg, 9.0%, three steps) as a yellow solid. $^1$H-NMR (CDCl$_3$) δ 8.28 (d, J=8.4, 1H), 8.24 (d, J=9.2, 1H), 6.70 (d, J=8.8, 1H), 6.59 (dd, J=2.0, 8.8, 1H), 6.54 (d, J=2.0, 1H), 5.28 (d, J=1.2, 1H), 4.18 (bs, 2H), 3.67 (s, 3H), 3.04 (s, 3H), 1.97 (d, J=1.2, 3H), 1.57 (s, 3H), 1.10 (s, 3H). ESI-MS m/z (M+H) calc'd: 334.2, found 334.1$^+$.

Example 14

Synthesis of
3-Amino-6-diethylamino-10H-acridin-9-one (K)

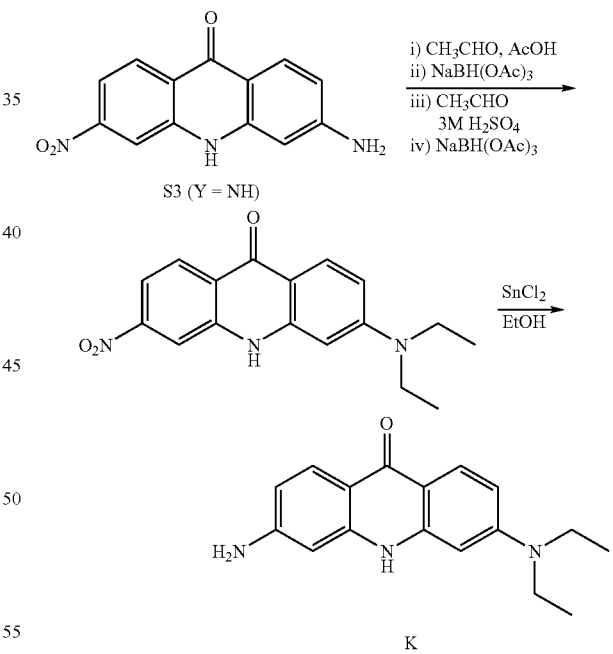

To a solution of S3 (2.7 g, 10.5 mmol) in DMF (15 mL) and 1,2-dichlroethane (40 mL), acetaldehyde (1.78 mL, 31.0 mmol) and acetic acid (3.63 mL, 63.0 mmol) were added. After stirring at room temperature for 1 hr, sodium triacetoxyborohydride (3.35 g, 15.8 mmol) was added and stirred overnight. The reaction mixture was diluted with dichloromethane and washed with aq. NaHCO$_3$, and brine. The combined organic layers were dried over sodium sulfate. The filtrate was concentrated and solidified in methanol. The filtered solid was dried under vacuum. The solid was dissolved in THF (100 mL), and added acetaldehyde (1.6 mL) and 3.5 M sulfuric acid (12.11 mL). After stirring for 1 hr, sodium triacetoxyborohydride (1.8 g) was added and stirred overnight. The reaction mixture was concentrated and basified with aq. 1N NaOH solution (pH 9-10). The resulting solid was filtered and dried under vacuum. The solid was reduced with tin chloride dihydrate, yielding K (300 mg, 10.1%, three steps) as a yellow solid. $^1$H-NMR (CDCl$_3$+CD$_3$OD) δ 8.14 (d, J=9.2, 1H), 8.10 (d, J=8.8, 1H), 6.68 (dd, J=2.4, 9.2, 1H), 6.58 (dd, J=2.0, 8.8, 1H), 6.44 (d, J=2.4, 1H), 6.36 (d, J=2.4, 1H), 3.48 (q, J=7.2, 4H), 1.25 (t, J=7.2, 6H). ESI-MS m/z (M+H) calc'd: 282.2, found 282.1.

Example 15

Synthesis of L (3-Amino-6-[(3-dimethylamino-propyl)-ethyl-amino]-xanthen-9-one)

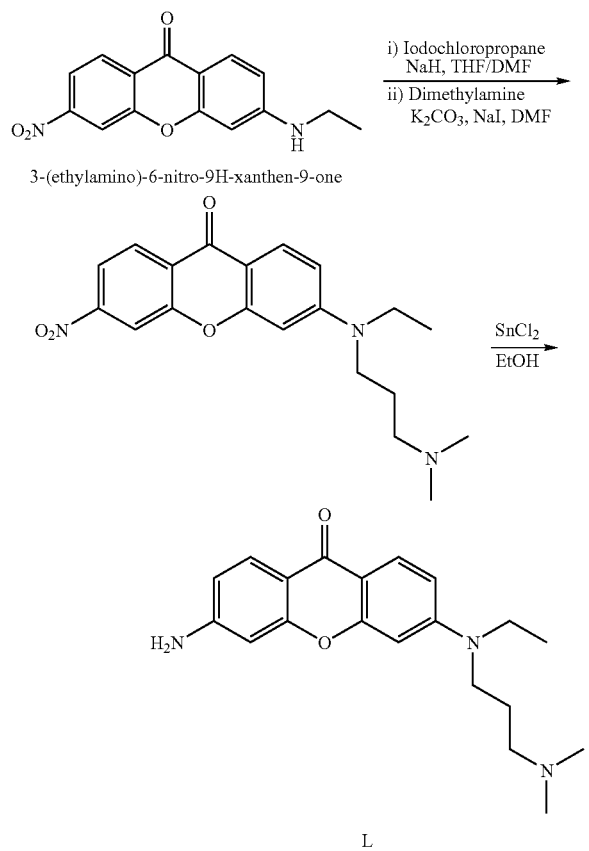

To a solution of 3-(ethylamino)-6-nitro-9H-xanthen-9-one (1.38 g, 4.86 mmol) in THF/DMF (50 mL/5 mL) was added sodium hydride (350 mg, 14.6 mmol) at 0° C. After stirring for 10 min, iodochloropropane (1.0 mL, 9.72 mmol) was added and warmed up slowly to room temperature while stirring overnight. The reaction mixture was diluted with dichloromethane and washed with 1N HCl, aq. NaHCO$_3$, and brine. The organic layer was dried over sodium sulfate, and the filtrate was concentrated and purified on silica gel column chromatography (ethyl acetate/hexane) to give the orange solid (690 mg, 39.3%). To the solid (640 mg, 1.78 mmol) in DMF (15 mL) was added potassium carbonate (490 mg, 3.56 mmol), sodium iodide (320 mg, 2.14 mmol), and dimethylamine (2 M in THF) (2.6 mL, 5.34 mmol). The reaction mixture was heated at 80° C. overnight, and all the solvents were evaporated under vacuum. The reaction mixture was dissolved in methanol and dichloromethane, the precipitating salts were removed by filtration, and the filtrate was concentrated and dried under vacuum. The crude mixture was treated with tin chloride to reduce nitro group reduction, yielding L as a yellow solid (210 mg, 34.7%, two steps). $^1$H-NMR (CD$_3$OD+CDCl$_3$) δ 8.03 (d, J=9.2, 1H), 7.96 (d, J=8.4, 1H), 6.74 (dd, J=3.4, 8.8, 1H), 6.66 (dd, J=2.0, 8.8, 1H), 6.56 (d, J=2.0, 1H), 6.53 (d, J=2.8, 1H), 3.52 (m, 4H), 2.81 (t, J=7.8, 2H), 2.59 (s, 6H), 1.99 (m, 2H), 1.26 (t, J=7.0, 3H). ESI-MS m/z (M+H) calc'd: 340.2, found 340.1.

Examples 16-19

General Procedure for Library Synthesis on Solid Support

Example 16

Preparation of 2-chlorotrityl Chloride from 2-chlorotrityl Alcohol Resin

2-Chlorotrityl alcohol resin (500 mg 1.37 mmol/g) was suspended in dichloromethane (5 mL) for 10 min. Thionyl chloride (150 µL, 2.06 mmol) was added, and the vial was shaken for 2 hours at room temperature. The resin was filtered, washed with dichloromethane and acetonitrile, and then dried.

Example 17

General Procedure for Loading A-L to Solid Resin

Each compound (A-L, the T$^1$ building blocks in Table 1) (0.411 mmol) was dissolved in dichloromethane (5 mL) using 20 mL vial, and, if not soluble, DMF was added (1-2 mL). The solution was added to a 2-chlorotrityl chloride resin (0.274 mmol) suspended in dichloromethane (1 mL), and pyridine (4.11 mmol) was added. After stirring for 4 hrs, the resin was filtered through 3 mL cartridge and washed with DMF (X5), methanol (X10), and dichloromethane (X10), and dried.

Example 18

General Procedure of Grignard Reaction and Cleavage from the Resin

For each reaction, a resin (10 mg) was suspended in freshly distilled THF (0.1 mL) in a 4 mL glass vial, and each Grignard reagent (0.5M in THF) (1.5 mL) was added and capped tightly with a TFE lined cap, and heated at 62-64° C. on standard heat-block for 2-4 days. The resin was filtered through 1 mL cartridge and washed with dichloromethane (X5), DMF (X5), methanol (X5), and dichloromethane (X5). The resin was dried and treated with 1% TFA in dichloromethane (1.5 mL) for 15 min, and the solution was drained to the 4 mL vial, and dried using SpeedVac.

Example 19

Modified Procedure for T$^1$ Building Block (D) Series

Compound D (from the list of building blocks T$^1$ in Table 1) was loaded on the resin as described, but was preceded by butyldimethylsilyl group protection. The resin was suspended in DMF, t-butyldimethylsilyl chloride (5 eq.) and imidazole (10 eq.) and stirred overnight. The solution was drained, and the resin was washed with DMF, methanol, and dichloromethane continuously. The dried resin was reacted with Grignard reagents, and the resin was cleaved as described above.

Example 20

Structure and HPLC Traces of Representative Compounds

The representative HPLC traces and mass spectra are illustrated in FIGS. 1 to 5 to show the purity and identity of each compound. All compounds were identified by LC-MS from Agilent Technology, using a C18 column (20×4.0 mm), with 4 minutes elution using a gradient solution of $CH_3CN$—$H_2O$ (containing 0.1% acetic acid), with UV detector and an electrospray ionization source. All of HPLC traces at 250 nm showed over 95% purity when calculated on the basis of the integration.

Example 21

Characterization of the Specific Rosamine Molecule A4

Absorption was taken using SpectraMax Plus absorbance plate reader, showing a maximum wavelength at 500 nm. Fluorescence emission was taken using Spectra Max Gemini XSF, giving a maximum wavelength at 530 nm. Molecule A4 showed a strong green fluorescence upon irradiation of 365 nm UV. See FIGS. 6A-D.

Example 22

Localization of Rosamine Molecules

3T3 cells were grown on the glass bottom, 96-well black plates, and each rosamine derivative compound is added to the cell culture to reach the desired concentration (500 nM to 5 µM) and incubated for half an hour. The optical fluorescence microscope was used for investigating the localization of each compound in the cell. Many of them have shown localization to mitochondria. Several examples of different localizations are selected and shown in FIG. 7.

Example 23

Screening of Rosamine Libraries

The rosamine derivative compounds were screened toward 47 different analytes that include proteins, polysaccharides, nucleic acids, and metal ions. The stock solution of each dye (50 µL) in HEPES (20 mM, pH=7.4) or PBS (20 mM, pH=7.4) was prepared, and diluted with the each analyte (50 µL, 1.0 mg/mL or 200 µM) in the same buffer solution. The final dye concentration varied from 0.5 µM to 10 µM. The fluorescence intensity fold changes of each dye in the presence of analytes were calculated by comparing the fluorescence intensity at the maximum emission wavelength with/without the analyte. The fold changes of all the compounds were summarized in FIG. 8.

Example 24

Fluorescence Emission Response of Molecule G13

Molecule G13 was screened for fluorescence intensity change toward 13 different macromolecules that include proteins, polysaccharides, and nucleic acids (i.e. HSA, BSA, dsDNA, RNA, peroxidase, cellulase A, protease A, lipase, lysozyme, papain, heparin, hemoglobin, and hemicellulase). Molecule G13 (10 µM) exhibited a highly selective fluorescence increase (12.5 fold change) toward human serum albumin (HSA). Interestingly, a very close protein, bovine serum albumin (BSA) showed only small response (1.5 fold change) to G13, with almost no change for all other proteins. See FIG. 9.

Example 25

In vitro Fluorescence Response of H22 to Glutathione (GSH)

Figure 12:
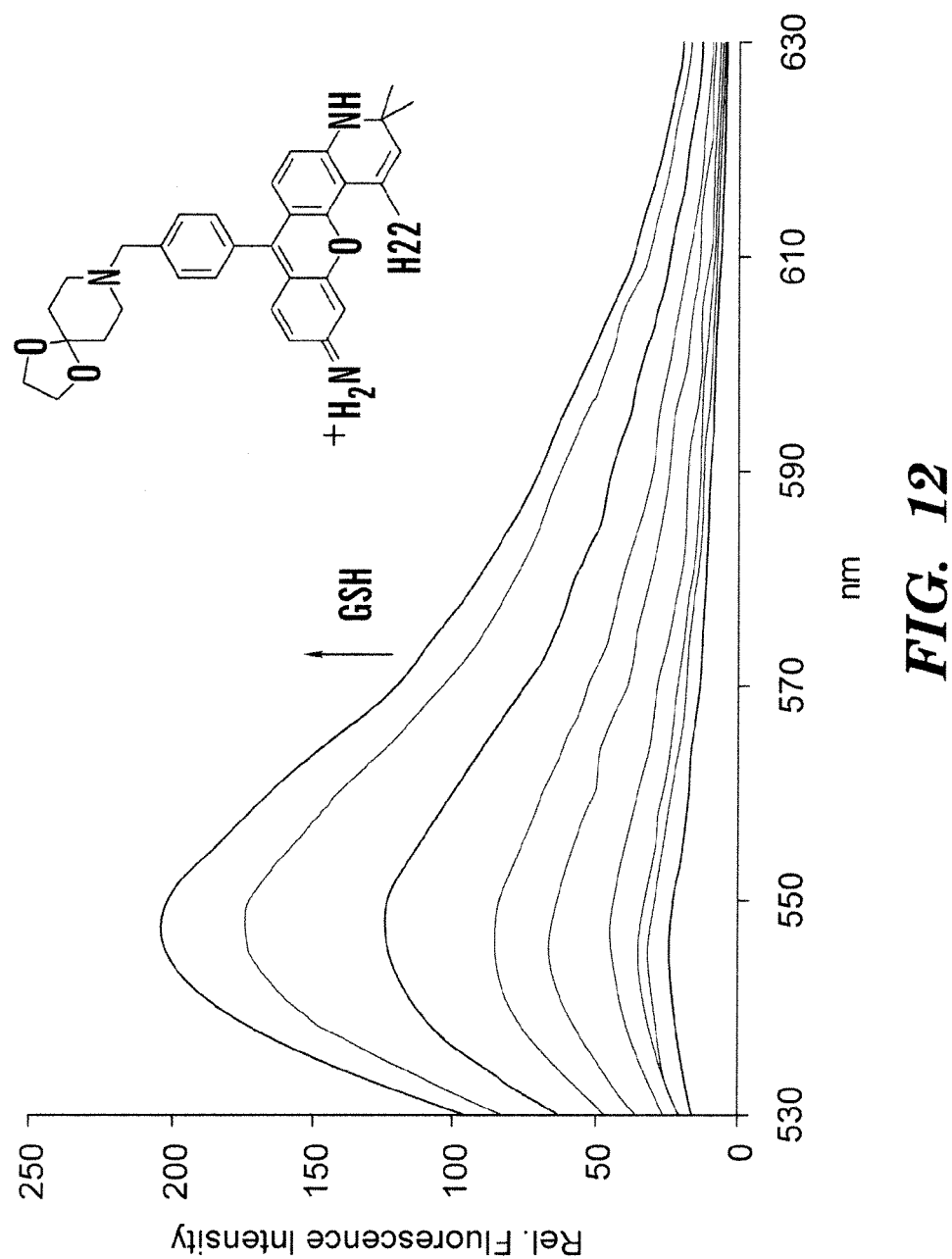
FIG. 12 shows the fluorescence responses of H22 in Table 1 (3 μM) toward GSH in 0, 0.01, 0.05, 0.1, 0.25, 0.5, 1.0, 2.5, 5 mM. H22 was incubated with GSH for 30 min in 50 mM HEPES, pH 7.4. Spectra were obtained with excitation at 500 nm.
Figure 13:
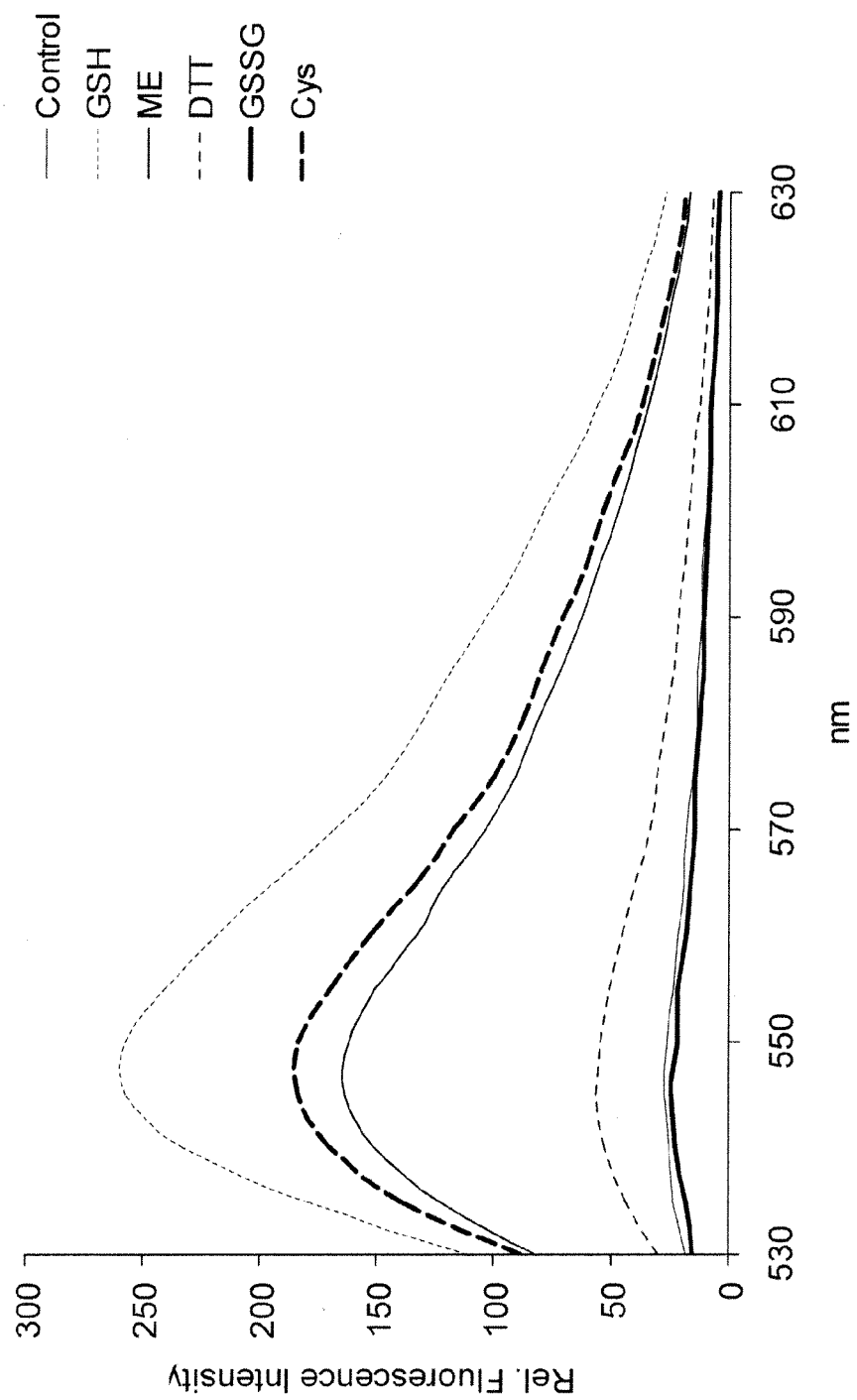
FIG. 13 shows the fluorescence responses of H22 in Table 1 (3 μM) toward GSSG and various thiols (5 mM) in 50 mM HEPES (pH 7.4) after 30 min incubation with excitation of 500 nm

Molecule H22 exhibited a highly selective response toward reduced glutathione (GSH). Under physiological conditions (pH 7.4, 50 mM HEPES), H22 (3 µM) showed a marked fluorescence increase upon addition of GSH (5 mM) by ca. 11-fold in 30 min (FIG. 12). H22 did not show any fluorescence response to GSSG (5 mM) while several thiol-containing analytes (5 mM) such as DTT, β-mercaptoethanol (ME) and cysteine showed modest responses to H22 (FIG. 13)

Example 26

Imaging in vivo Glutathione (GSH) with H22

Figure 14A:
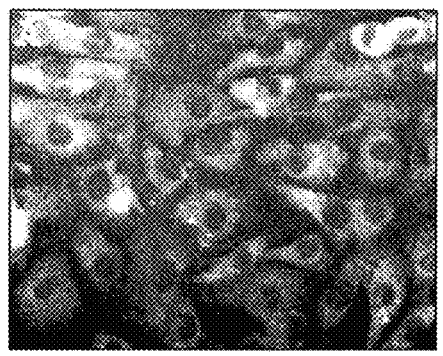
FIGS. 14A-D show the fluorescence microscopic images of live 3T3 cells stained with H22 in Table 1.
Figure 14B:
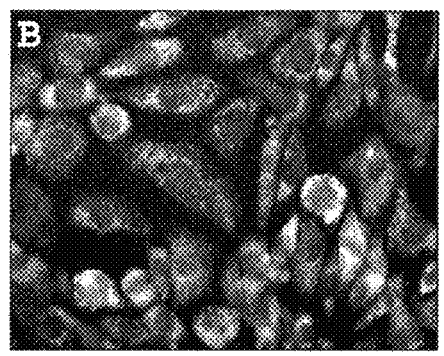
Figure 14C:
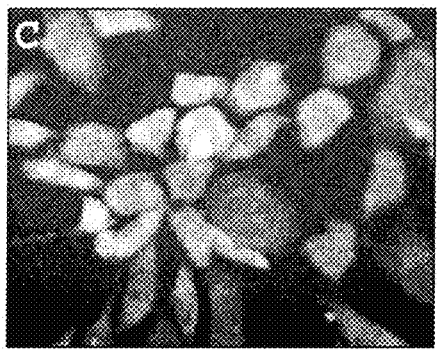
Figure 14D:
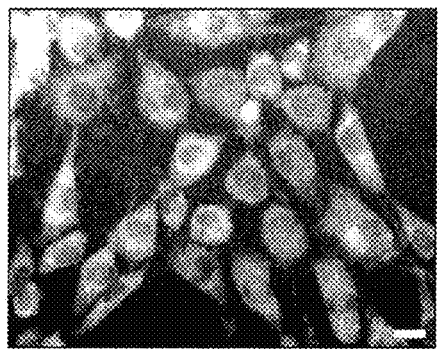

The capability of H22 to monitor GSH in a living cell was tested. α-Lipoic acid is known to enhance the reduced GSH level in a variety of cells. Thus, 3T3 cells were supplemented with α-lipoic acid (250 µM) for 48 hr. Subsequent staining of cells with H22 (3 µM) showed a clear increase in the intracellular fluorescence intensity in α-lipoic acid treated cells (FIG. 14B) compared to non-treated cells (FIG. 14A). When N-methylmaleimide (NMM, thiol reactive reagent: FIG. 14C) or diamide (thiol oxidant: FIG. 14D) was supplemented to α-lipoic acid-treated cells stained with H22, a distinct decrease of fluorescence intensity was observed.

Example 27

Monitoring the Glutathione (GSH) Depletion with H22

Figures 15A, 15B, 15C, 15D:
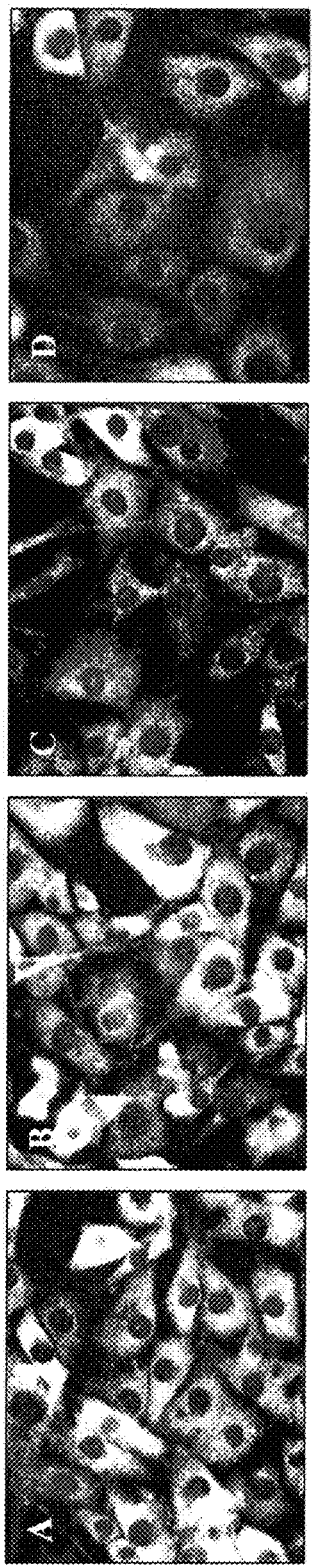
FIGS. 15A-D show the fluorescence images of 3T3 cells stained with H22 in Table 1 that monitored the GSH depletion upon treatment of BSO. 3T3 cells were stained with H22 (3 μM). Subsequently, a series of concentration of BSO was incubated for 60 min. 0 μM (FIG. 15A), 25 μM (FIG. 15B), 50 μM (FIG. 15C), 100 μM of BSO (FIG. 15D).

The GSH depletion was monitored by H22 when 3T3 cells were incubated with BSO (buthionine sulfoximine; GSH synthesis inhibitor). 3T3 cells were stained with H22 (3 µM). Subsequently, a series of concentration of BSO was incubated for 60 min, exhibiting a decrease of fluorescence intensity. See FIGS. 15A-D, which show the following BSO concentrations: 0 µM (FIG. 15A), 25 µM (FIG. 15B), 50 µM (FIG. 15C), and 100 µM (FIG. 15D).

Example 28

Fluorescence Emission Response of Molecule J and L

Figure 10A:
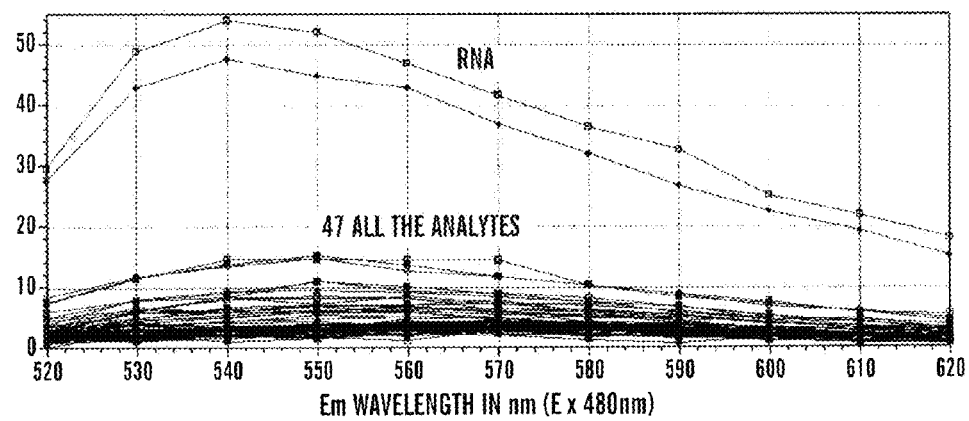
FIG. 10A shows the selective increase of fluorescence intensity of J in the presence of RNA, duplicated.
Figure 10B:
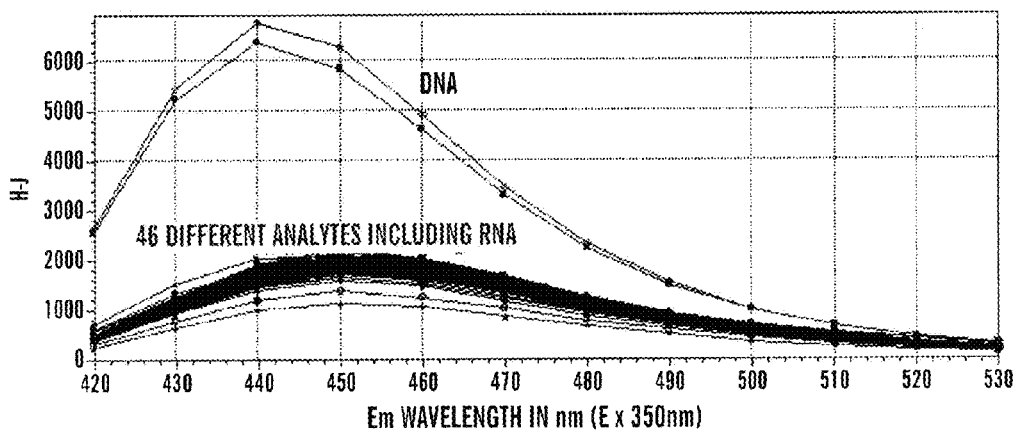
FIG. 10B shows the selective increase of fluorescence intensity of L in the presence of DNA, duplicated.

From the screening of rosamine libraries toward 47 different analytes that include proteins, polysaccharides, nucleic acids, and metal ions (FIG. 8), molecule J exhibited a selective response to RNA and molecule L showed a selective response to DNA (FIG. 10A-B).

Example 29

Absorbance, Fluorescent Wavelength, and Purity for the Library of Rosamine Derivative Compounds For the rosamine derivative compounds, all absorption data was obtained by a plate reader in PBS (10 mM). Purity data was calculated on the basis of the integration in the HPLC trace at 250 nm. Mass was calculated as (M$^+$) and found in ESI-MS m/e. Excitation ranges were from 480-545 nm and emission ranges were from 530-605 nm. See FIG. 11.

Example 30

Detection of Cell-State Switching

The design and synthesis of fluorescent compound libraries (Rosania et al., *Am. Chem. Soc.* 125:1130-1131 (2003) and Ahn et al., *Am. Chem. Soc.* 129:4510-4511 (2007), which are hereby incorporated by reference in their entirety) was inspired by the desire to screen for probes of cellular metabolites (Wang et al., *J Am. Chem. Soc.* 128:10380-10381 (2006); Lee et al., *Angew. Chem. Int. Ed.* 45:6485-6487 (2006), Li et al., *Chem. Biol.* 13:615-623 (2006), which are hereby incorporated by reference in their entirety). These studies were extended by performing parallel cell-based screening on a collection of 1606 optically active compounds, using both murine C2C12 myoblasts and differentiated myotubes. After incubating cells with compounds for 1 h at 37° C., the assay plates were washed and fluorescence measured using a multimode plate reader at two common wavelength pairs (485 nm/530 nm and 530 nm/580 nm). Using a scoring algorithm dependent upon the distribution of raw values from mock-treated wells (Kim et al., *J. Am. Chem. Soc.* 126:14740-14745 (2004), Franz et al., *J. Am. Chem. Soc.* 129:1020-1021 (2007), which are hereby incorporated by reference in their entirety), a normalized score was determined for each compound-treated well, representing the number of standard deviations from the mean of that distribution. In primary screening, the majority of compounds were positive outliers for cellular fluorescence at one wavelength in both cells states, suggesting either that these compounds have no cell-state selectivity, or that the concentration of compound used was so high as to mask selectivity by signal saturation.

Example 31

Cell Culture

C2C12 myoblasts (ATCC) were grown in Dulbecco's Modified Eagle Medium (DMEM, Mediatech) supplemented with 10% fetal bovine serum (FBS) and antibiotics (100 μg/mL penicillin/streptomycin mixture) in a humidified atmosphere at 37° C. with 5% $CO_2$. Differentiation into myotubes was induced at 80% density on "day 0" by changing media to DMEM supplemented with 2% horse serum (DM).

Example 32

High-throughput and High-content Screening for Cellular Fluorescence

For all screening experiments, 4000 C2C12 myoblasts were seeded per well of black 384-well optical bottom plates, at 50 μL/well. On day 4 of differentiation, 100 nL compound was pin-transferred in duplicate into fresh media with a steel pin array, using the CyBi-Well robot (CyBio, Woburn, Mass.). In order to increase the number of mock-treated wells included in the control distribution, an additional plate was added, which received DMSO alone by pin-transfer into each well. Mock- and compound-treated plates were incubated at 37° C. for 1-4 h, followed by cell fixation, staining of DNA with Hoechst 33342, and washing with PBS. All high-throughput cell-based assay measurements were performed using the EnVision plate reader (PerkinElmer, Waltham, Mass.). For high-throughput screening, ChemBank "Composite-Z" scores, reflecting compound performance as compared to a mock-treated (DMSO) distribution, were calculated essentially as described (Kim et al., "Relationship of Stereochemical and Skeletal Diversity to Cellular Measurement Space," *J. Am. Chem. Soc.* 126:14740-14745 (2004); Franz et al., "Synthesis and Cellular Profiling of Diverse Organosilicon Small Molecules," *J. Am. Chem. Soc.* 129: 1020-1021 (2007), which are hereby incorporated by reference in their entirety).

High-content screening involved treating the plates exactly as described above, with the exception of the measurements being taken by the ImageXpress IX5000A automated microscope (Molecular Devices; Sunnyvale, Calif.). Images from each well were acquired at 4× objective magnification at two wavelength pairs (485/530 nm, to detect compound fluorescence, and 360/460 nm, to detect nuclei). Exposure times were kept constant (DAPI channel 50 ms, FITC channel 25 ms) in order to prevent artificially increased fluorescence in the myoblast state, and to prevent saturation of high-intensity images. Gamma correction, with an exponent of 0.6, was applied to all DAPI images in MATLAB (The Mathworks; Natick, Mass.), primarily to linearize the relationship between color and signal. Linear transformations of brightness and contrast were applied in exactly the same way to all FITC images in Photoshop (Adobe Systems Inc.; San Jose, Calif.).

Example 33

High-throughput Screen for Myogenesis

Figures 19A, 19B:
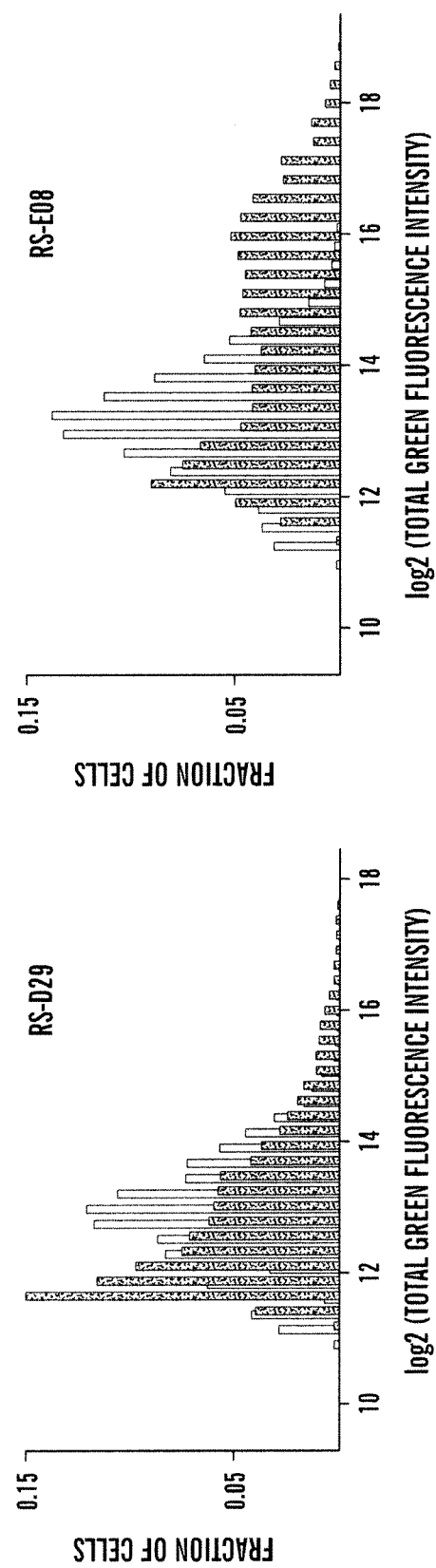
Figure 19C:
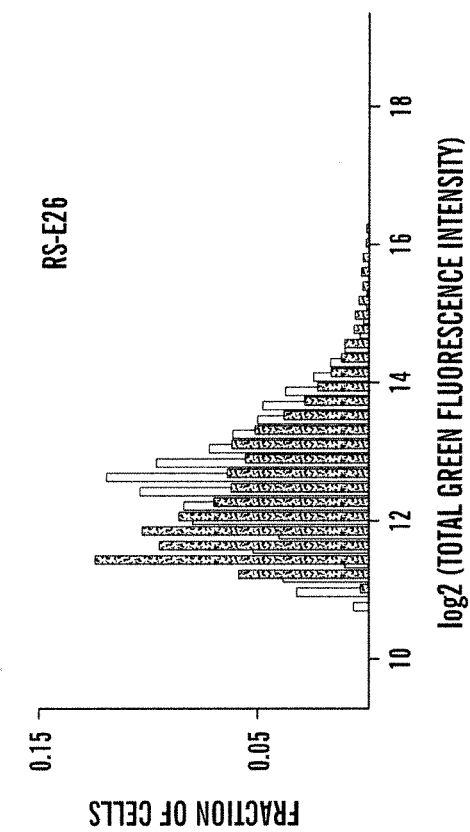
Figure 19D:
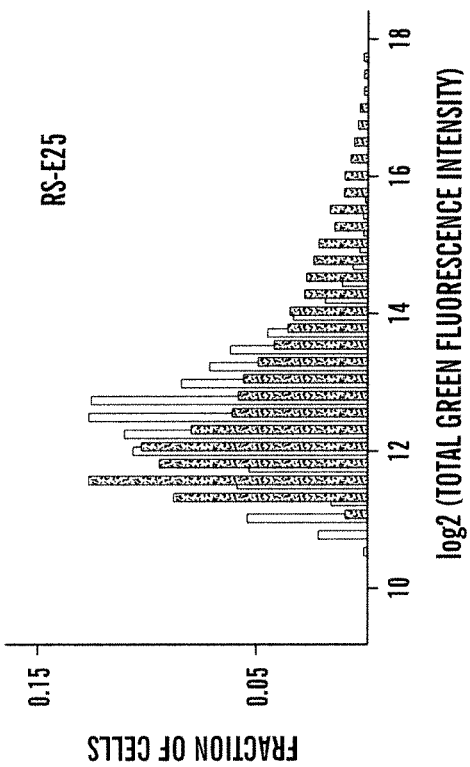
Figure 20D:
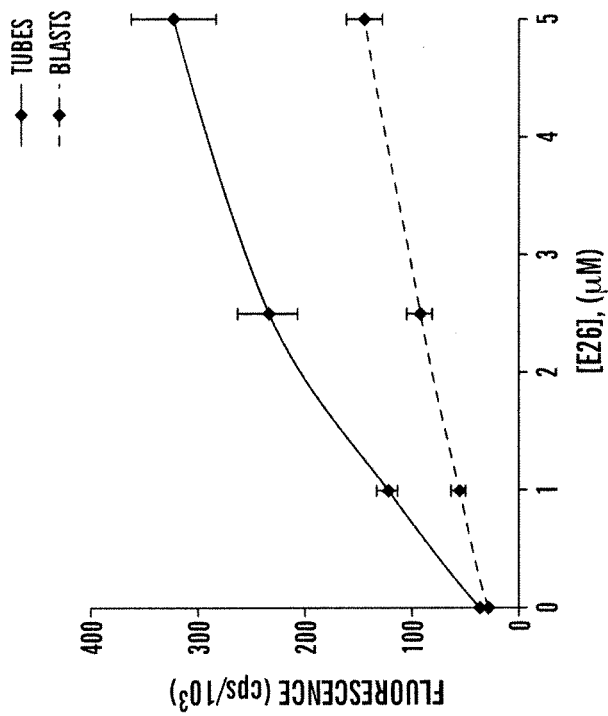
Figure 20C:
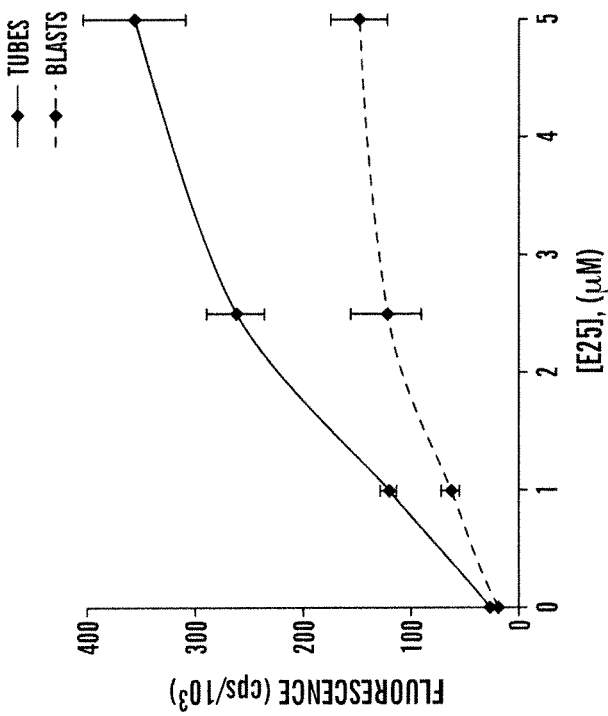
Figure 20E:
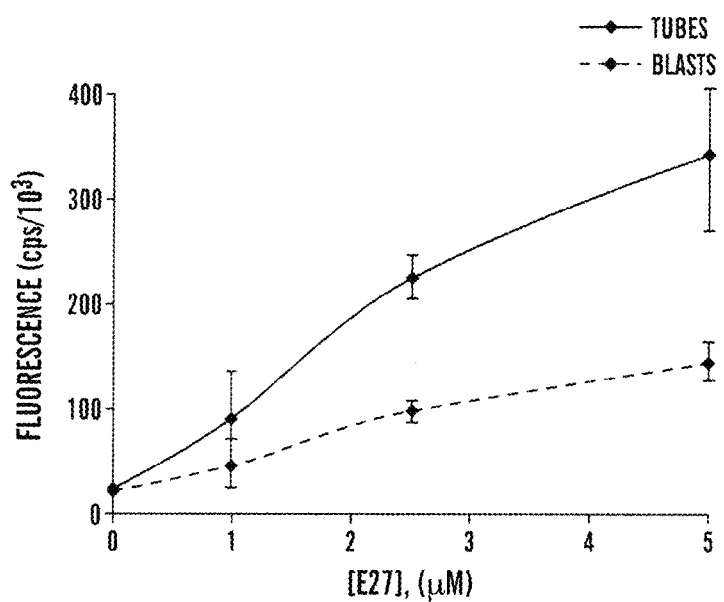
Figure 21A:
FIGS. 21A-D show representative two-color overlay images from myogenesis screening experiments. Cells were stained with 1 μM E26 (green), and DNA with Hoechst 33342 (blue).
Figure 21B:
Figure 21C:
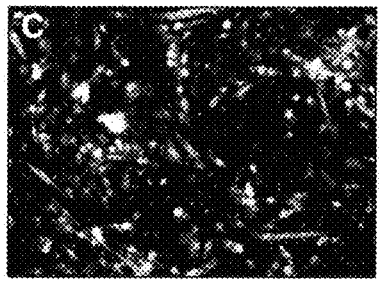
Figure 21D:
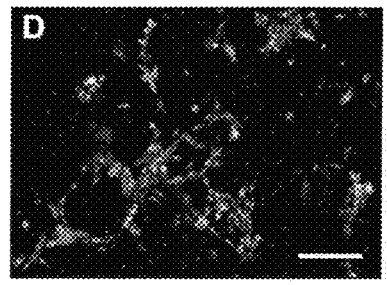

For myogenesis screening experiments, C2C12 myoblasts were cultured and seeded as described above. The following day, 100-nL stock-solutions of various commercially available kinase inhibitors were pin-transferred into the assay plates in the presence of DM. Cells were incubated with compounds for 48 h, then replaced with fresh compound-free DM. Cells were incubated for an additional 72 h, treated for 1 h with 1 μM E26 (see text), then fixed and washed as described above. Fluorescence was measured using the EnVision plate reader at 485/535 nm ($\lambda_{ex}/\lambda_{em}$). See FIGS. 18-20.

Example 34

High-throughput Screening for Myogenesis

As a result of plate-reader experiments, it was decided to use E26 as a screening agent, because it provided the greatest difference in fluorescence intensity between myoblasts and myotubes at 1 μM.

Quantitative data for high-throughput screening of the kinase inhibitor collection for inhibition of myogenesis carried out. Note that the rapamycin concentration shown in FIG. 19 was higher when used for staining by E26 (600 nM) than that used for MHC immunofluorescence (100 nM). This comparison was intended to be qualitative, and further studies are needed to quantify the relationship between E26 staining and MHC immunofluorescence. See FIG. 21.

In order to distinguish these possibilities, both myoblasts and myotubes were treated with a collection representing an 81-fold dilution of the original compounds, achieved by four serial three-fold dilutions. Cell-state selectivity was assessed by automated microscopy. At this lower concentration, many of the compounds were no longer fluorescent in either cell state. Alternatively, a few compounds continued to fluoresce in both cell states. However, six of the compounds had the desired result, with observable fluorescence exclusively in myotubes (FIGS. 16A-D and FIGS. 17A-F).

Figure 16A:
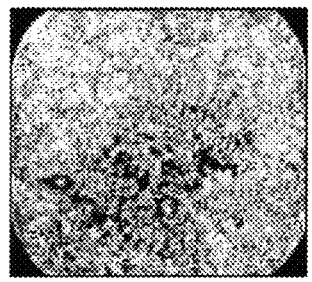
FIGS. 16A-E show the discovery of a myotube-specific fluorescent probe. C2C12 myoblasts (FIGS. 16A, B) or myotubes (FIGS. 16C, D) were treated with 250 nM E26 for 1 h following plating and differentiation, and imaged using an automated microscope. DNA was stained with Hoechst dye (FIGS. 16A, C) to confirm cell adherence, and imaged for E26 fluorescence (FIGS. 16B, D). Treatment of C2C12 myoblasts (dashed line) or myotubes (solid line) with increasing concentrations of E26 results in fluorescence detectable using a plate reader, displayed as thousands of counts per second (FIG. 16E). The mean and standard deviation of 48 wells for each condition are shown. Scale bar=150 μm.
Figure 16B:
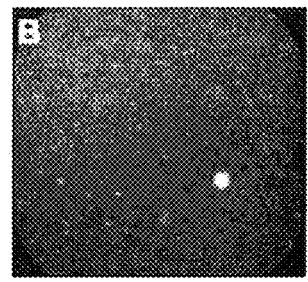
Figure 16C:
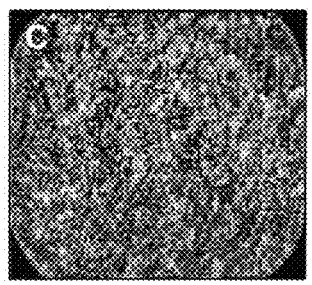
Figure 16D:
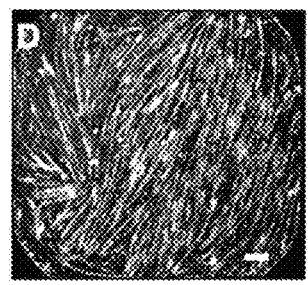
Figure 16E:
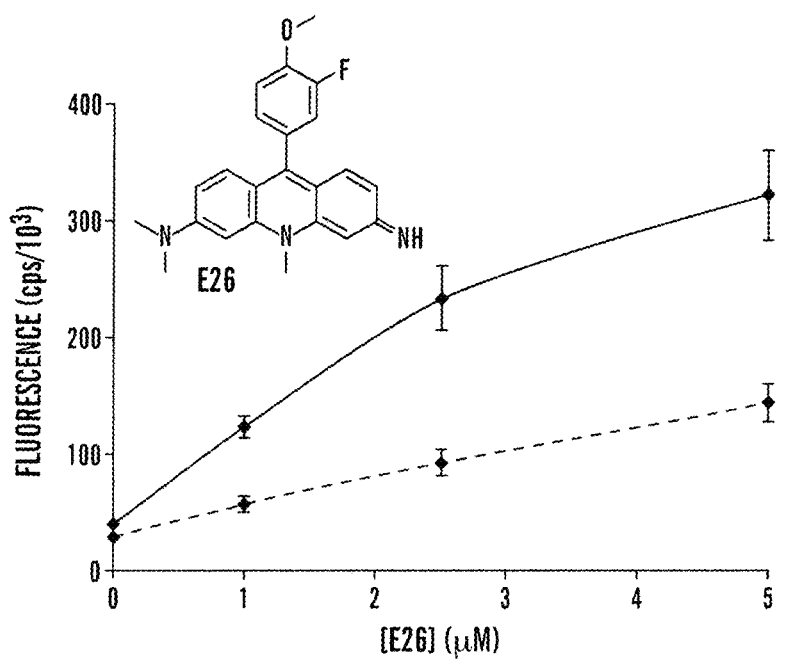
Figure 17D:
Figure 17F:
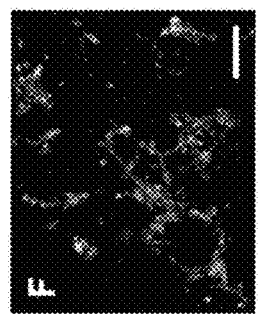
Figure 17C:
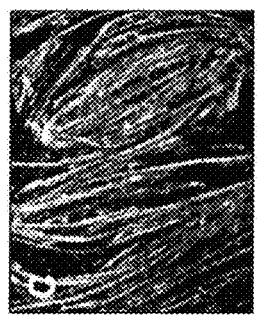
Figure 17E:
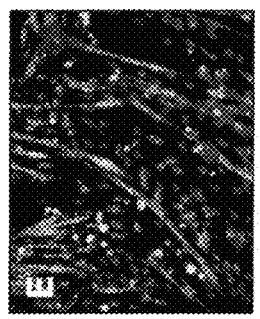
Figure 18B:
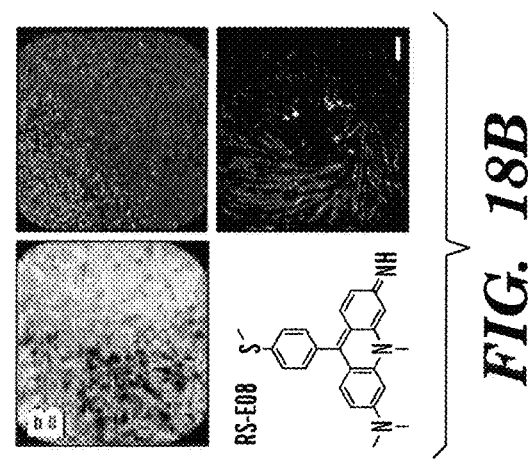
FIGS. 18A-F show representative images from high-content screening of rosamine (RS) library. Compounds were screened at 250 nM to detect cell type specificity: compound D29 (FIG. 18A), compound E08 (FIG. 18B), compound E25 (FIG. 18C), compound E26 (FIG. 18D), compound E27 (FIG. 18E), and compound E23 (FIG. 18F). For each panel, the images represent compound fluorescence in myoblasts (upper right), compound fluorescence in myotubes (lower right), identity and chemical structure of each compound (lower left), and nuclei of myoblasts (upper left), showing that wells of myoblasts and myotubes each contained comparable densities of nuclei. Scale bars=150 μm.
Figure 18A:
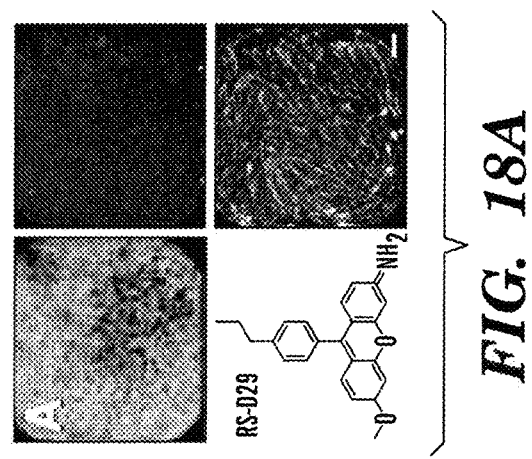
Figure 18C:
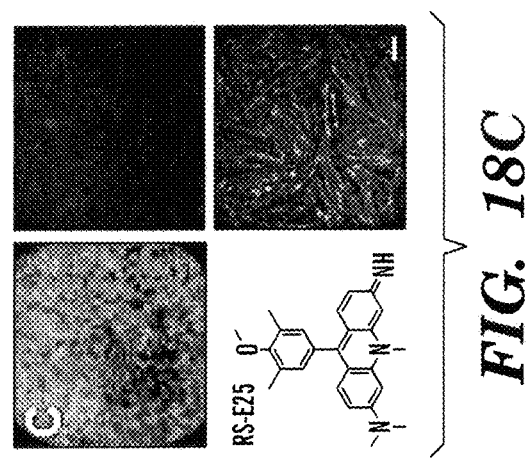
Figure 18D:
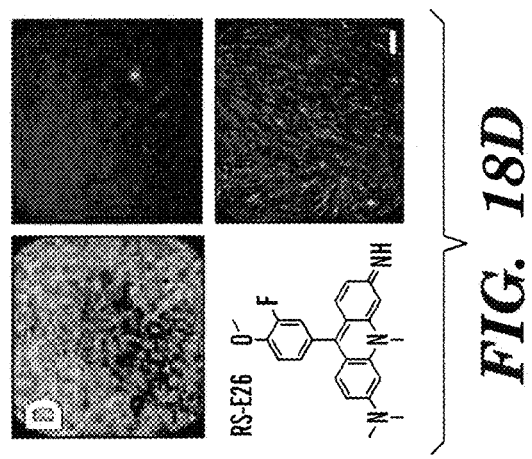
Figure 18F:
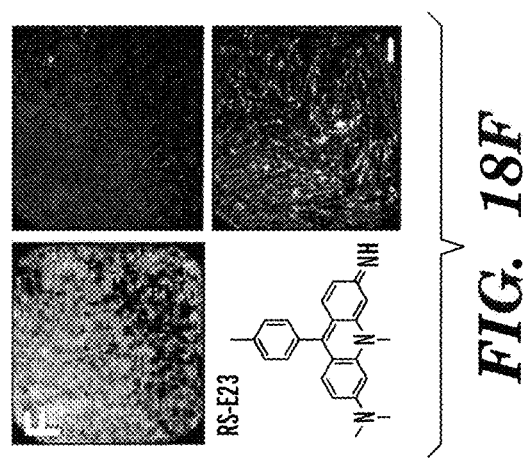
Figure 18E:
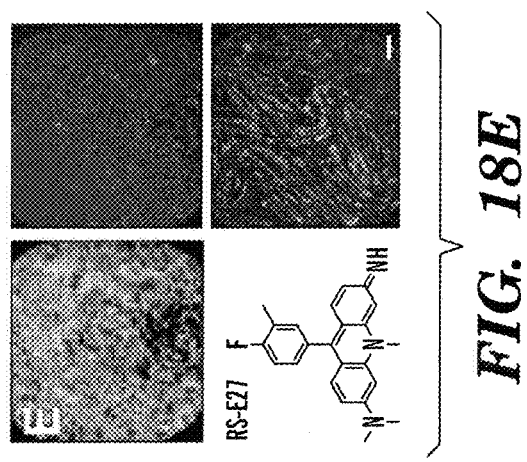

One of the goals of determining the cell-state selectivity of compound fluorescence is to use these compounds as probes for high-throughput screening. In order to demonstrate the utility of these compounds, differential cellular fluorescence was confirmed using a multimode plate reader (FIG. 16E) after treating 384-well plates of cells with varying concentrations of compound for 1 h. 1 μM E26 was used as a probe for myogenesis, thus balancing maximal signal difference with minimal compound use, in a pilot screen of eighty-four kinase inhibitors, plated at four doses each in a 384-well stock plate. Two 384-well plates of C2C12 myoblasts were treated with these compounds in differentiation media containing 2% horse serum for two days, followed by three further days of culture in differentiation media without compound. These plates of cells with E26 were treated in the same manner as during assay development. Seventeen of the eighty-four compounds, including known inhibitors of myogenesis (Conejo et al., *J. Cell. Physiol.* 186:82-94 (2001) and Hribal et al., *Accili* 162:535-541 (2003), which are hereby incorporated by reference in their entirety), significantly p<0.05; see SI) inhibited differentiation at one or more concentrations (FIG. 17A). Kinase inhibitors known to induce apoptosis in myoblasts, such as staurosporine (McArdle et al., *J. Lab. Invest.* 79:1069-1076 (1999), which is hereby incorporated by reference in its entirety), also reduced the fluorescent signal to a significant extent (FIG. 17B). The results from compound E26 with immunofluorescent staining of myosin heavy chain (MHC) were compared for the ability to detect the effects of rapamycin on myogenesis. In both treatments, myotubes fluoresced brightly (FIGS. 17C, 17E). Rapamycin is capable at concentrations as low as 10 nM of inhibiting differentiation of C2C12 myoblasts (Erbay et al., *J. Biol. Chem.* 276:36079-36082 (2001) and Shu et al., *J. Biol. Chem.* 277:16726-16732 (2002), which are hereby incorporated by reference in their entirety), and a similar decrease in cellular fluorescence was observed with either MHC antibody-based staining (FIG. 17D) or E26 treatment (FIG. 17F). These results suggest that E26 is a reliable fluorescent probe for use in cell-based screening for myogenesis. Cell-state selectivity of this compound may be achieved by binding to one of the many proteins expressed more highly in the myotube state (Miller, J. B., *J. Cell. Biol.* 111: 1149-1159 (1990), which are hereby incorporated by reference in their entirety). Alternatively, there may be an environmental effect within the myotube that promotes compound retention or fluorescence. While further study is necessary to determine the mechanism of cell-state selectivity, these observations are sufficient to confirm that such selectivity exists and can be leveraged for screening purposes. The strategy of screening reported here may be extended more broadly in the future.

Although the invention has been described in detail, for the purpose of illustration, it is understood that such detail is for that purpose and variations can be made therein by those skilled in the art without departing from the spirit and scope of the invention which is defined by the following claims.

What is claimed:

1. A method of distinguishing, in a sample, distinct states resulting from cellular differentiation in forms of a cell type of interest and one or more differentiated forms of the cell type of interest, said method comprising:
   providing a sample containing a cell type of interest and one or more differentiated forms of the cell type of interest;
   providing a rosamine derivative compound of the formula:

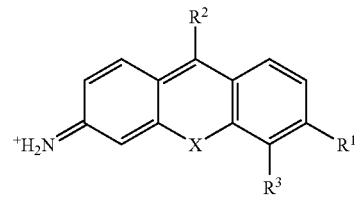

wherein:
   X is O, NR$^4$, or S;
   R$_1$ is NR$^4$R$^5$, OH, NR$^4$R$^6$, or

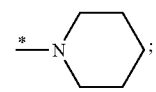

R$^2$ is substituted or unsubstituted phenyl, napthyl,

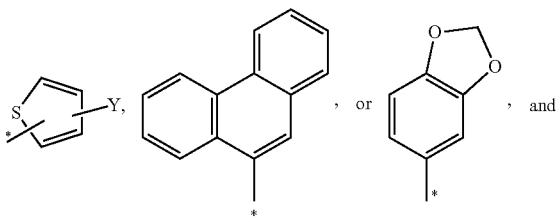

wherein the substituted form of R$^2$ has one or more substituents independently selected from the group consisting of halogen, NR$^4$R$^5$, OR$^7$, SR$^4$, aryl, C$_1$ to C$_6$ alkyl,

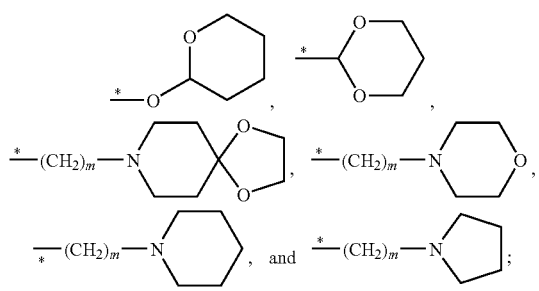

R$^3$ is H or with R$^1$ collectively forms a fused ring of the structure of

R⁴ is H or C₁ to C₆ alkyl;
R⁵ is H, C₁ to C₆ alkyl, or with R⁴ collectively forms a ring structure;
R⁶ is $(CH_2)_n NR^4R^8$;
R⁷ is H, C₁ to C₆ alkyl, or aryl;
R⁸ is H or C₁ to C₆ alkyl;
Y is alkyl or halogen;
n is 1 to 3;
m is 0 to 3; and
* is a site on a substituent which binds to the rosamine derivative compound, wherein the rosamine compound produces differing fluorescent signals for the cell type of interest than for the one or more differentiated forms of the cell type of interest;
contacting the sample with the rosamine derivative compound under conditions effective to produce differing fluorescent signals for the cell type of interest than for the one or more differentiated forms of the cell type of interest; and
detecting and distinguishing, as distinct states resulting from cellular differentiation, the presence of the cell type of interest and the presence of one or more differentiated forms of the cell type of interest based on fluorescent signals emitted by the sample following said contacting.

2. The method of claim 1, wherein X is O.
3. The method of claim 1, wherein X is NR⁴.
4. The method of claim 1, wherein X is S.
5. The method of claim 1, wherein R¹ is NR⁴R⁵.
6. The method of claim 1, wherein R¹ is OH.
7. The method of claim 1, wherein R¹ is NR⁴R⁶.
8. The method of claim 1, wherein R¹ is 9. The method of claim 1, wherein the rosamine compound is 10. The method of claim 1, wherein the cell type of interest and the one or more differentiated forms of the cell type of interest being distinguished from one another are selected, respectively, from the group consisting of: myoblasts and myotubes; neural stem cells and neurons, astrocytes, oligodendrocytes; mesenchymal stem cells and osteoblasts, chondrocytes, myocytes, adipocytes; endocrine progenitor cells and pancreatic cell types, including alpha and beta cells.

11. The method of claim 10, wherein the cell type of interest and the one or more differentiated forms of the cell type of interest are myoblasts and myotubes, respectively.

12. A method of screening for compounds which inhibit differentiation of a cell type of interest to one or more differentiated forms of the cell type of interest, said method comprising:
providing a sample containing a cell type of interest;
providing a rosamine derivative compound of the formula:

wherein:
X is O, NR⁴, or S;
R₁ is NR⁴R⁵, OH, NR⁴R⁶, or

R² is substituted or unsubstituted phenyl, napthyl, wherein the substituted form of R² has one or more substituents independently selected from the group consisting of halogen, NR⁴R⁵, OR⁷, SR⁴, aryl, C₁ to C₆ alkyl, -continued

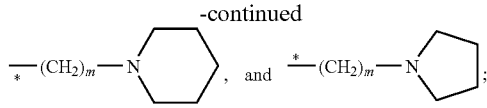

$R^3$ is H or with $R^1$ collectively forms a fused ring of the structure of

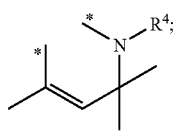

$R^4$ is H or $C_1$ to $C_6$ alkyl;
$R^5$ is H, $C_1$ to $C_6$ alkyl, or with $R^4$ collectively forms a ring structure;
$R^6$ is $(CH_2)_n NR^4R^8$;
$R^7$ is H, $C_1$ to $C_6$ alkyl, or aryl;
$R^8$ is H or $C_1$ to $C_6$ alkyl;
Y is alkyl or halogen;
n is 1 to 3;
m is 0 to 3; and
* is a site on a substituent which binds to the rosamine derivative compound, wherein the rosamine compound produces differing fluorescent signals for the cell type of interest than for the one or more differentiated forms of the cell type of interest;
providing a candidate compound;
contacting the sample, the candidate compound, and the rosamine derivative compound;
subjecting the sample, prior to or after said contacting, to conditions effective to cause the cell type of interest in the sample to undergo differentiation to the one or more differentiated forms of the cell type of interest; and
identifying candidate compounds which reduce fluorescent signal for differentiated forms of the cell type of interest as having potential activity as inhibitors of differentiation of the cell type of interest.

13. The method of claim 12, wherein X is O.
14. The method of claim 12, wherein X is $NR^4$.
15. The method of claim 12, wherein X is S.
16. The method of claim 12, wherein $R^1$ is $NR^4R^5$.
17. The method of claim 12, wherein $R^1$ is OH.
18. The method of claim 12, wherein $R^1$ is $NR^4R^6$.
19. The method of claim 12, wherein $R^1$ is

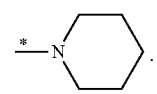

20. The method of claim 12, wherein the rosamine compound is

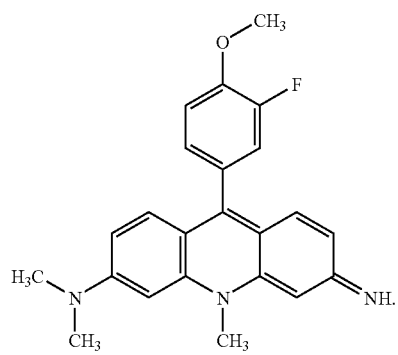 [SMILES: COc1ccc(-c2c3ccc(=N)cc-3n(C)c3cc(N(C)C)ccc23)cc1F]

21. The method of claim 12, wherein the cell type of interest and the one or more differentiated forms of the cell type of interest are selected, respectively, from the group consisting of: myoblasts and myotubes; neural stem cells and neurons, astrocytes, oligodendrocytes; mesenchymal stem cells and osteoblasts, chondrocytes, myocytes, adipocytes; endocrine progenitor cells and pancreatic cell types, including alpha and beta cells.

22. The method of claim 12, wherein the cell type of interest and the one or more differentiated forms of the cell type of interest are myoblasts and myotubes, respectively.

* * * * *